(12) United States Patent
Arukuusk et al.

(10) Patent No.: US 12,385,042 B2
(45) Date of Patent: Aug. 12, 2025

(54) CELL-PENETRATING PEPTIDES

(71) Applicant: VECTIOPEP OÜ, Tartu Maakond (EE)

(72) Inventors: Piret Arukuusk, Tartu (EE); Ülo Langel, Tartu (EE); Ly Porosk, Tartu (EE)

(73) Assignee: VECTIOPEP OÜ, Tartu Maakond (EE)

( * ) Notice: Subject to any disclaimer, the term of this patent is extended or adjusted under 35 U.S.C. 154(b) by 1070 days.

(21) Appl. No.: 17/421,605

(22) PCT Filed: Jan. 10, 2020

(86) PCT No.: PCT/EP2020/050524
§ 371 (c)(1),
(2) Date: Jul. 8, 2021

(87) PCT Pub. No.: WO2020/144317
PCT Pub. Date: Jul. 16, 2020

(65) Prior Publication Data
US 2022/0186215 A1 Jun. 16, 2022

(30) Foreign Application Priority Data
Jan. 11, 2019 (GB) .................................... 1900443

(51) Int. Cl.
| | | |
|---|---|---|
| A61K 47/64 | (2017.01) | |
| A61K 47/54 | (2017.01) | |
| C12N 15/11 | (2006.01) | |
| C12N 15/87 | (2006.01) | |

(52) U.S. Cl.
CPC .......... *C12N 15/111* (2013.01); *A61K 47/542* (2017.08); *A61K 47/6455* (2017.08); *C12N 15/87* (2013.01); *C12N 2310/14* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

2014/0038281 A1\* 2/2014 Langel ................... C12N 15/87
530/300
2014/0206596 A1 7/2014 Shen et al.

FOREIGN PATENT DOCUMENTS

EP 2491952 A1 8/2012

OTHER PUBLICATIONS

Freimann, K., et al., "Optimization of in vivo DNA delivery with NickFect peptide vectors", Journal of Controlled Release, 2016, vol. 241, pp. 135-143.
Regberg, J., et al., "pH-responsive PepFect cell-penetrating peptides," International Journal of Pharmaceuticals, 2016, vol. 501, pp. 32-38.
Chu, D., et al., "Rational modification of oligoarginine for highly efficient siRNA delivery: structure-activity relationship and mechanism of intracellular trafficking of siRNA," Nanomedicine: Nanotechnology Biology & Medicine, 2015, vol. 11, pp. 435-446.
Pan, R., et al., "A novel peptide for efficient siRNA delivery in vitro and therapeutics in vivo," Acta Biomaterialia, 2015, vol. 21, pp. 74-84.
Okada, H., "Targeted siRNA therapy using cytoplasm-responsive nanocarriers and cell-penetrating peptides," Journal of Korean Pharmaceutical Sciences, 2014, vol. 44, No. 7, pp. 505-516.
Alhakamy, N.A., et al., "Noncovalenty associated cell-penetrating peptides for gene delivery applications," Therapeutic Delivery, 2013, vol. 4, No. 6, pp. 741-757.
Nakase, I.,et al., "Efficient Intracellular Delivery of Nucleic Acid Pharmaceuticals Using Cell-Penetrating Peptides," Accounts of Chemical Research, 2012, vol. 45, No. 7, pp. 1132-1139.
Ferrer-Miralles, N., et al., "Biological activities of histidine-rich peptides; merging biotechnology and nanomedicine," Microbial Cell Factories, 2011, vol. 10, No. 1, p. 101.
Porosk , L., et al., "Enhancement of siRNA transfection by the optimization of fatty acid length and histidine content in the CPP," Biomaterials Science, Royal Society of Chemistry, 2019, vol. 7, No. 10, pp. 4363-4374.
Yao, J., et al., "Design of new acid-activiated cell-penetrating peptides for tumor drug delivery," PeerJ, 2017, vol. 5, e3429.
Pärnaste, L., et al., "The Formation of Nanoparticles between Small Interfering RNA and Amphipathic Cell-Penetrating Peptides," Molecular Therapy: Nucleic Acids, 2017, vol. 7, pp. 1-10.
Erazo-Oliveras, A., et al., "Improving the Endosomal Escape of Cell-Penetrating Peptides and Their Cargos: Strategies and Challenges," Pharmaceuticals, 2012, vol. 5, No. 11, pp. 1177-1209.
Lehto, T., et al., "Saturated Fatty Acid Analogues of Cell-Penetrating Peptide PepFect14: Role of Fatty Acid Modification in Complexation and Delivery of Splice-Correcting Oligonucleotides, " Bioconjugate Chemistry, 2017, vol. 28, No. 3, pp. 782-792.

\* cited by examiner

*Primary Examiner* — Ronald T Niebauer
(74) *Attorney, Agent, or Firm* — Hoffmann & Baron, LLP

(57) ABSTRACT

The present invention provides for a membrane-permeable construct for transport of cargo across a lipid membrane and subsequent delivery of cargo into cells, wherein the construct comprises a cell penetrating amino acid sequence and a fatty acid chain attached to the N terminus thereof, wherein the cell penetrating amino acid sequence comprises the sequence of SEQ ID NO: 1, or comprises a modified sequence of SEQ ID NO: 1, wherein the cell penetrating amino acid sequence comprises two or more histidine residues by substitution to its N-terminal part and/or addition to its N-terminus, and wherein the cell penetrating amino acid sequence is optionally chemically modified at the C terminus.

11 Claims, 16 Drawing Sheets
Specification includes a Sequence Listing.

B

CELL-PENETRATING PEPTIDES

CROSS REFERENCE TO RELATED APPLICATIONS

The present application is a National Stage Application claiming priority from co-pending PCT Application No. PCT/EP2020/050524 filed Jan. 10, 2020, which in turn claims priority from Great Britain Application Serial No. 1900443.1 filed Jan. 11, 2019. Applicants claim the benefits of 35 U.S.C. § 120 as to the said PCT application, and priority under 35 U.S.C. § 119 as to the said Great Britain application, and the entire disclosures of all applications are incorporated herein by reference in their entireties.

FIELD OF THE INVENTION

The present invention relates inter alia to a membrane-permeable construct for transport of cargo across a lipid membrane and subsequent delivery of cargo into cells. The present invention also relates to therapeutic uses of such a construct, for example in the treatment of cancer.

BACKGROUND

Cell penetrating amino acid sequences (also referred to as cell penetrating peptides or "CPPs") are relatively short peptides that have the ability to gain access into the cell and mediate the delivery of cargo covalently or non-covalently attached to them.

Small interfering RNA (siRNA) molecules regulate the expression of specific genes in the cells through a process called RNA interference (RNAi). The use of an unmodified extracellular siRNA is limited due to its native properties such as high density of negative charges, inadequate permeability through the cell membrane and high susceptibility to degradation in the intra- and extracellular environment. These RNA molecules have a great therapeutic potential although their use could be significantly enhanced by the application of a suitable delivery method or the use of modifications in the siRNA itself.

Cell penetrating amino acids have been used to deliver a multitude of different molecules including, but not limited to, siRNAs. The cell penetrating amino acids sequences typically contain several positively charged amino acids (arginine, lysine, histidine and non-proteogenic amino acid ornithine) and are thus able to associate with the negatively charged backbone of nucleic acid. They form a non-covalent complex mainly via electrostatic interactions, although hydrophobic interactions may play a role in the stability of the formed complexes. The non-covalent cell penetrating amino acid sequence/cargo complexation strategy allows for a simple complex formation with a high mixing versatility, but the limitations of using this approach may include heterogeneity and low stability of the complexes, and the premature or limited dissociation of the cargo from the complexes.

When associated with a cargo, the cell penetrating amino acid sequence/cargo complexes mainly enter via endosomal pathways and end up in the endosomal compartments or in the lysosomes. In order to take its intended effect, the internalization has to be promptly followed by the release of complexes from these organelles.

The cell membrane has an amphiphilic nature. To enhance cell penetrating amino acid membrane interactions, several cell penetrating amino acid sequences have been designed to have both hydrophilic and hydrophobic regions and/or moieties in their sequence. NickFect55 (NF55) is a cell penetrating peptide, useful as a plasmid DNA (pDNA) delivery vector for nucleic acid delivery applications in vitro and in vivo. It has an N-terminal fatty acid and a non-proteinogenic amino acid, ornithine in the $aa_7$ position. It was initially designed for the delivery of pDNA with an optimal CPP/pDNA complex stability and positive charges distributed along theoretical alpha-helix. Several amphipathic CPPs have been used to efficiently deliver siRNAs into the mammalian cells.

There is a need to provide more efficient cell delivery systems, to delivery associated cargo from the extracellular environment to the intracellular environment.

SUMMARY OF THE INVENTION

The Inventors have surprisingly found that the constructs of the present invention have good pH sensitivity and are good at delivery of cargo into the intracellular compartment. In particular, the constructs are sensitive to changes in pH which allows for efficient cell delivery of cargo via endosomes.

Advantageously, it is expected that the constructs may be used for targeted cancer therapy in tumours where the cancer and cancer microenvironment has a low pH. Further, in at least some embodiments, the constructs of the present invention are more effective for cell cargo delivery, preferably for oligonucleotide delivery, more preferably for siRNA delivery. In at least some embodiments the constructs are more effective at siRNA delivery than existing cell penetrating peptides, for example PF6 or NF55.

The constructs of the present invention also in at least some embodiments advantageously have low toxicity and are expected to be cheaper to synthesise compared to existing cell penetrating peptides, for example PF6 or NF55.

Thus, in a first aspect of the present invention, there is provided a membrane-permeable construct for transport of cargo across a lipid membrane and subsequent delivery of cargo into cells, wherein the construct comprises a cell penetrating amino acid sequence and a fatty acid chain attached to the N terminus thereof, wherein the cell penetrating amino acid sequence comprises the sequence of SEQ ID NO: 1, or comprises the sequence of SEQ ID NO: 1 having one or more modifications selected from:
  (i) an N9L amino acid substitution;
  (ii) an A14K amino acid substitution;
  (iii) a deletion of the alanine residue at position 1 or a deletion of the alanine residue at position 1 and a deletion of the glycine residue at position 2;
  (iv) a substitution of the ornithine residue at position 7 with Dab or Dap; and
  (v) one or two amino acid substitutions at positions 9 to 21 of SEQ ID NO: 1 in addition to or instead of N9L and/or A14K, wherein the cell penetrating amino acid sequence comprises two or more histidine residues by substitution to its N-terminal part and/or addition to its N-terminus, and wherein the cell penetrating amino acid sequence is optionally chemically modified (e.g. amidated) at the C terminus (e.g. the C terminus is $CONH_2$).

In another aspect of the present invention, there is provided a complex comprising the construct of the invention and a cargo non-covalently interacting therewith (e.g. interacting via ionic interactions).

In a further aspect of the present invention, there is provided a pharmaceutical composition comprising the construct or complex of the invention and a pharmaceutically acceptable carrier.

In yet a further aspect of the present invention, there is provided a method of treating cancer in an individual comprising administering an effective amount of the pharmaceutical composition of the invention to an individual.

In another aspect of the present invention, there is provided a method of gene silencing in an individual comprising administering an effective amount of the complex of the invention to the individual.

BRIEF DESCRIPTION OF THE SEQUENCES

Figure 1:
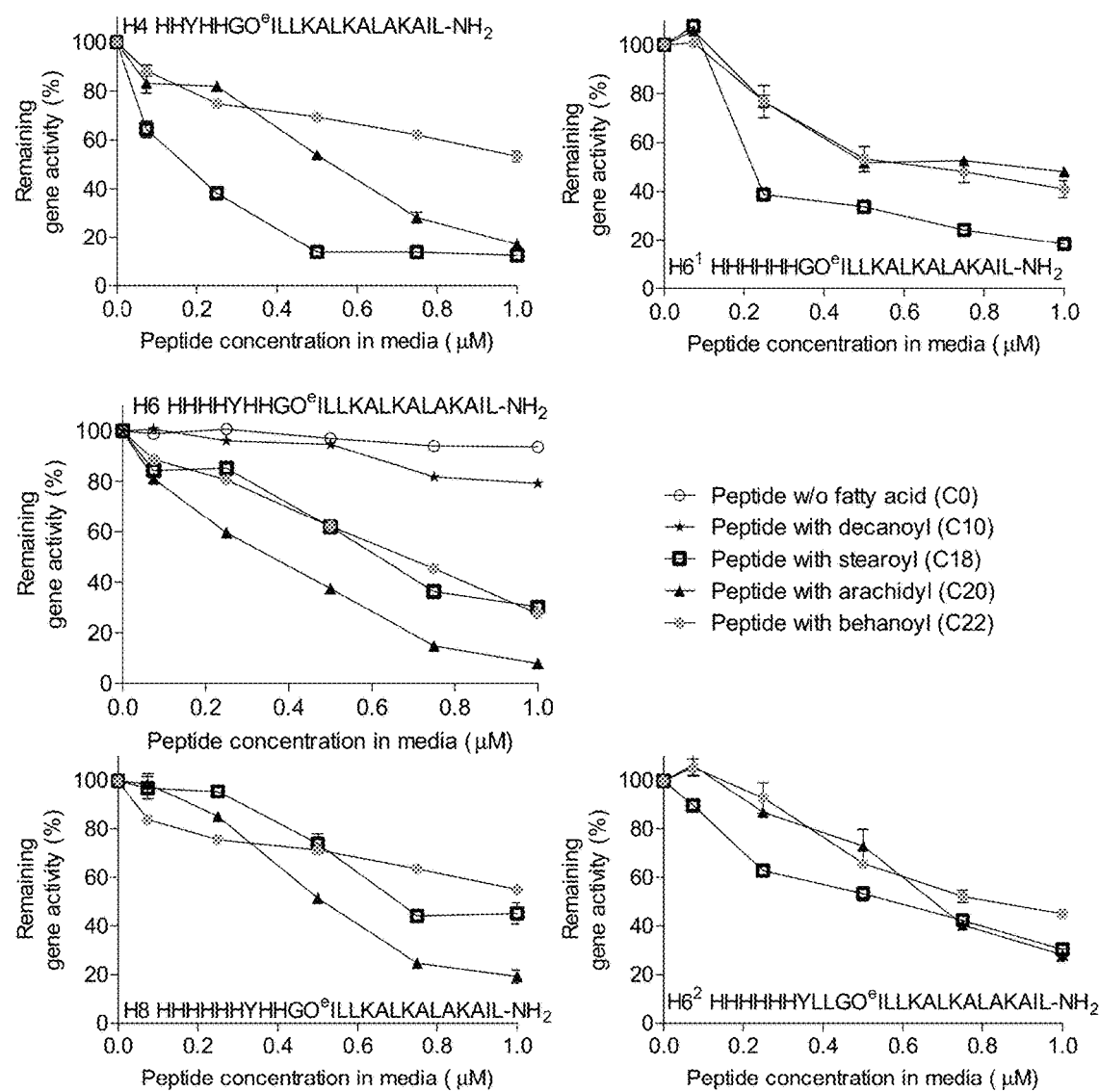
FIG. 1 shows the remaining gene activity after transfection with CPP/siRNA complexes containing siRNA against luciferase. Remaining gene activity is shown for each of: HHYHHGORILLKALKALAKAIL (SEQ ID NO:2), HHHHHHGORILLKALKALAKAIL (SEQ ID NO: 4), HHHHYHHGO$^e$ILLKALKALAKAIL (SEQ ID NO:3), HHHHHHYHHGO$^e$ILLKALKALAKAIL (SEQ ID NO:5) and HHHHHHYLLGO$^e$ILLKALKALAKAIL (SEQ ID NO: 15). Results are normalised to protein content and untreated cells (100%).

SEQ ID NO: 1 encodes the wild-type amino acid sequence of NickFect55 (NF55).
SEQ ID NO: 2 encodes a cell penetrating amino acid sequence of the invention; NF71, NF712, NF713, NF717.
SEQ ID NO: 3 encodes a cell penetrating amino acid sequence of the invention; NF70, NF703, NF702, NF701, NF700, NF711.
SEQ ID NO: 4 encodes a cell penetrating amino acid sequence of the invention; NF704, NF705, NF706.
SEQ ID NO: 5 encodes a cell penetrating amino acid sequence of the invention; NF72, NF721, NF722.

SEQ ID NO: 6 encodes the general formula of an embodiment of the cell penetrating amino acid sequence of the invention.
SEQ ID NO: 7 encodes siRNA sense strand against luc2.
SEQ ID NO: 8 encodes siRNA antisense strand against luc2.
SEQ ID NO: 9 encodes the siRNA sense strand against GFP.
SEQ ID NO: 10 encodes the siRNA antisense strand against GFP.
SEQ ID NO: 11 encodes Mus blood coagulation factor VII forward PCR primer.
SEQ ID NO: 12 encodes Mus blood coagulation factor VII reverse PCR primer.
SEQ ID NO: 13 encodes Mus Actin beta forward PCR primer.
SEQ ID NO: 14 encodes Mus Actin beta reverse PCR primer.
SEQ ID NO: 15 encodes a cell penetrating amino acid sequence; NF707, NF708, NF709.
SEQ ID NO: 16 encodes a cell penetrating amino acid sequence of FIG. 12; NF714.
SEQ ID NO: 17 encodes a cell penetrating amino acid sequence of FIG. 12; NF73.
SEQ ID NO: 18 encodes a cell penetrating amino acid sequence of FIG. 12; NF74.
SEQ ID NO. 19 encodes a cell penetrating amino acid sequence of the invention; NF725, NF726, NF727.
SEQ ID NO. 20 encodes a cell penetrating amino acid sequence of the invention; NF715, NF716, NF718.
SEQ ID NO. 21 encodes a cell penetrating amino acid sequence of the invention; NF719, NF723, NF724.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only and is not intended to be limiting.

In addition, as used in this specification and the appended claims, the singular forms "a", "an", and "the" include plural referents unless the content clearly dictates otherwise. Thus, for example, reference to "an inhibitor" includes two or more such inhibitors, or reference to "an oligonucleotide" includes two or more such oligonucleotide and the like.

All publications, patents and patent applications cited herein, whether supra or infra, are hereby incorporated by reference in their entirety.

Construct

The term construct comprises a peptide of any length with a fatty acid chain attached. The construct may also further comprise a cargo.

The construct is membrane-permeable. The construct may pass from the extracellular environment across or through a membrane into the cell or intracellular environment. Membranes may be single or multiple layer structures. The construct may transport the cargo across a membrane and deliver the cargo into the cytoplasm of the cell. The construct may transport the cargo across a membrane and deliver the cargo to an organelle in the cell. The construct may transport cargo across a membrane and deliver the cargo to an intracellular surface. The construct may enter the cell via an endosomal pathway. The construct may be encapsulated in an intra-organelle, preferably in an endosomal compartment or in a lysosome, and subsequently be released into the intracellular compartment or environment.

The membrane may be an artificial membrane such as an artificially constructed complex membrane formed of, for example, lipids, phospholipids or molecules having both hydrophilic and hydrophobic compounds or structures. The membrane may be a biological membrane including but not limited to eukaryotic cell membranes and prokaryotic cell membranes. The membrane may be a lipid bilayer or phospholipid bilayer. The membrane may be a lipid membrane of a phospholipid membrane. The membrane may be a plasma membrane. Eukaryotic cell membranes include, but are not limited to, membranes of immune cells such as white blood cells, red blood cells, monocytes, macrophages, neutrophils, T cells, B cells or dendritic cells, epithelial cells, endothelial cells, keratinocytes, muscle cells, skin cells, nerve cells and fat cells.

Cell Penetrating Amino Acid Sequence

Cell penetrating amino acid sequences, also referred to as cell penetrating peptides or "CPPs", are short amino acid sequences that transport different types of cargo molecules across a lipid membrane and facilitate cellular uptake of the cargo molecules. Cell penetrating amino acid sequences may comprise between 20 to 25 or 25 to 30 amino acids. Cell penetrating amino acid sequences may comprise 20 or more, 21 or more, 22 or more, 23 or more, 24 or more, 25 or more, 26 or more, 27 or more, 28 or more, 29 or more, or 30 or more amino acids. Cell penetrating amino acid sequences may comprise 20, 21, 22, 23, 24, 25, 26, 27, 28, 29 or 30 amino acids.

A property of cell penetrating amino acids is their ability to translocate the lipid membrane and facilitate the delivery of various molecular cargoes to the cytoplasm or to an organelle of a cell or to an intracellular cell surface.

In an embodiment of the present invention, the cell penetrating amino acid sequence comprises SEQ ID NO: 1. In a further embodiment of the present invention, the cell penetrating amino acid sequence comprises SEQ ID NO: 1 having one or more modifications selected from:
   i) an N9L amino acid substitution;
   (ii) an A14K amino acid substitution;
   (iii) a deletion of the alanine residue at position 1 or a deletion of the alanine residue at position 1 and a deletion of the glycine residue at position 2;
   (iv) a substitution of the ornithine residue at position 7 with Dab or Dap; and
   (v) one or two amino acid substitutions at positions 9 to 21 of SEQ ID NO: 1 in addition to or instead of N9L and/or A14K,
wherein the cell penetrating amino acid sequence comprises two or more histidine residues by substitution to its N-terminal part and/or addition to its N-terminus, and wherein the cell penetrating amino acid sequence is optionally chemically modified (e.g. amidated) at the C terminus (e.g. the C terminus is $CONH_2$).

Dab refers to 2,4-diaminobutanoic acid. Dap refers to 2,3-diaminopropionic acid.

In another embodiment of the present invention, the cell penetrating amino acid sequence comprises SEQ ID NO: 1 or comprises the sequence of SEQ ID NO: 1 having one or more modifications selected from:
   i) an N9L amino acid substitution;
   (ii) an A14K amino acid substitution;
   (iii) a deletion of the alanine residue at position 1 or a deletion of the alanine residue at position 1 and a deletion of the glycine residue at position 2; and (iv) a substitution of the ornithine residue at position 7 with Dab or Dap,
wherein the cell penetrating amino acid sequence comprises two or more histidine residues by substitution to its N-terminal part and/or addition to its N-terminus, and wherein the cell penetrating amino acid sequence is optionally chemically modified (e.g. amidated) at the C terminus (e.g. the C terminus is $CONH_2$).

The cell penetrating amino acid sequence herein after refers to the cell penetrating amino acid sequence of the invention. The natural proteogenic amino acids are in the naturally occurring L-enantiomer configuration and the non-natural amino acids are also in the L-enantiomer configuration.

In an embodiment, the cell penetrating amino acid sequences of the invention have or comprise the amino acid sequence:

(SEQ ID NO: 6)

$H_n$YHHGO$^e$ILLKALKALAKAIL $^e$ Indicates that the Peptide Continues from the Side Chain Amino Group and not from the a-Amino Group The variable n refers to the number of histidine residues and n may equal one, two, three, four, five, six, seven, eight, nine or ten, preferably one, two, three, four, six, eight or ten, more preferably two, three, four, six, eight or ten, especially two, four, six, eight or ten.

In the foregoing text, a position number in the cell penetrating amino acid sequence refers to a position in the sequence by reference to the numbering of SEQ ID NO: 1, it being understood that the said sequence may have the modifications described herein. Substitution refers to the replacement of an amino acid with another different amino acid.

The cell penetrating amino acid sequence may have a N9L amino acid substitution and/or an A14K amino acid substitution and/or a deletion of the alanine residue at position 1 or a deletion of the alanine residue at position 1 and a deletion of the glycine residue at position 2 and/or a substitution of the ornithine residue at position 7 with Dab or Dap and/or one or two amino acid substitutions at positions 9 to 21 of SEQ ID NO: 1 in addition to or instead of N9L and/or A14K. In an embodiment of the invention, the cell penetrating amino acid sequence does not comprise one or two amino acid substitutions at positions 9 to 21 of SEQ ID NO: 1 in addition to or instead of N9L and/or A14K.

The N-terminal part of the cell penetrating amino acid sequence refers to the amino acids at positions 1 to 6 of the cell penetrating amino acid sequence, preferably amino acids at positions 1 to 5. Histidine residues referred to herein as "N-terminal histidine residues" are those present in the N-terminal part of the cell penetrating amino acid sequence. For example, the N-terminal part of SEQ ID NO: 1 refers to the amino acids at positions 1 to 6 of SEQ ID NO: 1, preferably amino acids at positions 1 to 5 of SEQ ID NO: 1. The N-terminal part of the cell penetrating amino acid sequence may also include amino acids at positions 1 to 4, 1 to 3, 1 to 2, 2 to 6, 2 to 5, 2 to 4, 2 to 3, 3 to 6, 3 to 5 and 3 to 4 of the cell penetrating amino acid sequence.

The cell penetrating amino acid sequence may comprise two or more histidine residues by substitution to its N-terminal part. In a preferred embodiment of the invention, two or more of the wild type amino acids in the N-terminal part of the cell penetrating peptide amino acid sequence of the invention are substituted or replaced with two or more histidine residues. Two or more, three or more, four or more, five or more, or six of the wild type amino acids in the N-terminal part of the cell penetrating peptide amino acid sequence are substituted or replaced with two or more, three or more, four or more, five or more, six histidine residues. The cell penetrating amino acid sequence may comprise two, three, four, five or six histidine residues in the N-terminal part.

The N-terminus of the cell penetrating amino acid sequence normally refers to the amino acid at position 1 of the amino acid sequence. For example, the N-terminus of SEQ ID NO: 1 refers to the amino acid at position 1 of SEQ ID NO: 1. When the amino acid at position 1 is deleted, however, the N-terminus refers to the amino acid at position 2 of the amino acid sequence. When the amino acids at positions 1 and 2 are deleted, the N-terminus refers to the amino acid at position 3 of the amino acid sequence. The N-terminus refers to the first amino acid present in the amino acid sequence of the cell penetrating peptide amino acid sequence.

The cell penetrating amino acid sequence may comprise one or more histidine residues added to the N terminus of the cell penetrating amino acid sequence. In a preferred embodiment of the invention, two or more histidine residues are added to the N terminus of the cell penetrating amino acid sequence. One or more, two or more, three or more, four or more, five or more, six or more, seven or more, or eight or more histidine residues may be added to the N-terminus of the cell penetrating amino acid sequence. Histidine residues referred to herein as "N-terminus histidine residues" are those added to the N-terminus of the cell-penetrating amino acid sequence.

In an embodiment of the present invention, the cell penetrating amino acid sequence comprises between three and eight histidine residues substituted in its N-terminal part and/or added at its N-terminus, preferably three, four, five, six or eight histidine residues. The cell penetrating amino acid sequence may comprise one, two, three, four, five, six, seven, eight, nine or ten histidine residues substituted in its N-terminal part and/or added at its N-terminus.

The cell penetrating amino acid sequence may comprise histidine amino acid substitutions at positions four and/or five, preferably at positions four and five of the cell penetrating amino acid sequence. The cell penetrating amino acid sequence may comprise histidine amino acid substitutions at positions four and/or five, preferably at positions four and five, when the amino acids at positions one and/or two are deleted.

In an embodiment of the present invention, the cell penetrating amino acid sequence comprises at least three histidine residues in its N-terminal part and/or added to its N terminus, arranged such that one histidine residue is substituted at position two of SEQ ID NO: 1, two histidine residues are substituted at positions four and five of SEQ ID NO: 1 and optionally one or more histidine residues are added to its N-terminus.

In another embodiment of the present invention, the cell penetrating amino acid sequence comprises three histidine residues in its N-terminal part, arranged such that one histidine residue is substituted at position two of SEQ ID NO: 1 and two histidine residues are substituted at positions four and five of SEQ ID NO: 1.

In a further embodiment of the present invention, the cell penetrating amino acid sequence comprises at least four histidine residues in its N-terminal part and/or added to its N terminus, arranged such that two histidine residues are substituted at positions one and two of SEQ ID NO: 1, two histidine residues are substituted at positions four and five of SEQ ID NO: 1 and optionally one or more histidine residues are added to its N-terminus.

In yet a further embodiment of the present invention, the cell penetrating amino acid sequence comprises four histidine residues in its N-terminal part, arranged such that two histidine residues are substituted at positions one and two of SEQ ID NO: 1 and two histidine residues are substituted at positions four and five of SEQ ID NO: 1.

In another embodiment of the present invention, the cell penetrating amino acid sequence comprises four histidine residues in its N-terminal part, arranged such that two histidine residues are substituted at positions one and two of SEQ ID NO: 1, two histidine residues are substituted at positions four and five of SEQ ID NO: 1 and also one histidine residue is added to its N-terminus.

In yet another embodiment of the present invention, the cell penetrating amino acid sequence comprises four histidine residues in its N-terminal part, arranged such that two histidine residues are substituted at positions one and two of SEQ ID NO: 1, two histidine residues are substituted at positions four and five of SEQ ID NO: 1 and also two histidine residues are added to its N-terminus.

In a further embodiment of the present invention, the cell penetrating amino acid sequence comprises four histidine residues in its N-terminal part, arranged such that two histidine residues are substituted at positions one and two of SEQ ID NO: 1, two histidine residues are substituted at positions four and five of SEQ ID NO: 1 and also four histidine residues are added to its N-terminus.

In yet a further embodiment of the present invention, the cell penetrating amino acid sequence comprises at least five histidine residues in its N-terminal part and/or added to its N terminus, arranged such that five histidine residues are substituted at positions one to five of SEQ ID NO: 1, and optionally one or more histidine residues are added to its N-terminus.

In another embodiment of the present invention, the cell penetrating amino acid sequence comprises five histidine residues in its N-terminal part, arranged such that five histidine residues are substituted at positions one to five of SEQ ID NO: 1 and also one histidine residue is added to its N-terminus.

The cell penetrating amino acid sequence may have the sequence encoded by any one of SEQ ID NO: 2, SEQ ID NO: 3, SEQ ID NO: 4 and SEQ ID NO: 5

Fatty Acids

A fatty acid is a carboxylic acid with a long aliphatic chain which is either saturated or unsaturated. Short chain fatty acids are fatty acids with aliphatic tails of five or fewer carbon atoms. Medium chain fatty acids are fatty acids with aliphatic tails of six to twelve carbon atoms. Long chain fatty acids are fatty acids with aliphatic tails of 13 to 21 carbon atoms. Very long chain fatty acids are fatty acids with aliphatic tails of 22 carbon atoms or more.

The fatty acid chain of the present invention may be a saturated carbon chain or an unsaturated carbon chain, but preferably is a saturated carbon chain. Saturated fatty acids have no carbon to carbon double bonds. Unsaturated fatty acids have one or more (e.g. one to four such as one or two) carbon to carbon double bonds. The carbon to carbon double bonds can give either cis or trans isomers.

A cis configuration means that two hydrogen atoms adjacent to the double bond protrude out on the same side of the chain. The rigidity of the double bond freezes its conformation and in the case of the cis isomer, causes the chain to bend and restricts the conformational freedom of the fatty acid. The more double bonds the chain has in the cis configuration, the less flexibility it has.

A trans configuration means that the adjacent two hydrogen atoms lie on opposite sides of the chain. Consequently, they do not cause the chain to bend much, and their shape is similar to straight saturated fatty acids.

A saturated fatty acid chain having 16 carbon atoms is also referred to as palmitic acid. A saturated fatty acid chain having 18 carbon atoms is also referred to as stearic acid. A saturated fatty acid chain having 20 carbon atoms is also referred to as arachidic acid. A saturated fatty acid chain having 22 carbon atoms is also referred to as behenic acid.

An example of an unsaturated fatty acid having 16 carbon atoms is palmitoleic acid or sapienic acid. An example of an unsaturated fatty acid having 18 carbons atoms is oleic acid or elaidic acid. An example of an unsaturated fatty acid having 20 carbon atoms is arachidonic acid or eicosapentaenoic acid. An example of an unsaturated fatty acid having 22 carbon atoms is erucic acid or docosahexaenoic acid.

The cell penetrating amino acid sequence has a fatty acid chain attached thereto. The fatty acid chain may also be referred to as a fatty acid moiety. The fatty acid chain is attached to the amino acid sequence or peptide by a covalent bond. The fatty acid chain may be attached to the peptide via a linker molecule. In a preferred embodiment of the invention, the fatty acid is attached to the N terminus of the cell penetrating amino acid sequence.

A linker may separate the peptide and the fatty acid chain. The linker may be a chemical moiety that contains two reactive groups/functional groups, one of which can react with the peptide and the other with the fatty acid chain. The two reactive/functional groups of the linker are linked via a linking moiety or spacer wherein the linking moiety or spacer does not interfere with the coupling of the linker to the peptide and the fatty acid chain. The linker can be made up of amino acids linked together by peptide bonds.

The fatty acid chain may have 16 to 22 carbon atoms, 16 to 20 carbon atoms, 16 to 18 carbon atoms, 16 carbon atoms, 18 to 22 carbon atoms, 18 to 20 carbon atoms, 18 carbon atoms, 20 to 22 carbon atoms, 20 carbon atoms or 22 carbon atoms. The fatty acid chain preferably has 18 carbon atoms or 20 carbon atoms.

In an embodiment of the present invention, the construct is selected from SEQ ID NO: 2 and a fatty acid chain having 18 carbon atoms, e.g, wherein the fatty acid is stearyl.

In another embodiment of the present invention, the construct is selected from SEQ ID NO: 2 and a fatty acid chain having 20 carbon atoms, e.g, wherein the fatty acid is arachidyl.

In yet another embodiment of the present invention, the construct is selected from SEQ ID NO: 3 and a fatty acid chain having 20 carbon atoms, e.g, wherein the fatty acid is arachidyl.

In a further embodiment of the present invention, the construct is selected from SEQ ID NO: 4 and a fatty acid chain having 18 carbon atoms, e.g, wherein the fatty acid is stearyl.

In yet a further embodiment of the present invention, the construct is selected from SEQ ID NO: 5 and a fatty acid chain having 20 carbon atoms, e.g, wherein the fatty acid is arachidyl.

Cargo

A cargo molecule may be a substance associated with a cell penetrating peptide intended to be transported into a cell. The cargo molecule may be associated with the cell penetrating peptide either through chemical linkage via covalent bonds or through non-covalent bond or ionic bonds or non-covalent interactions or ionic interactions. The cargo associated with the cell penetrating peptide may be transported from outside of the cell, across the membrane of the cell and enter into the cell. The cargo may then be released into the cytoplasm of the cell, directed to an intracellular organelle or presented at the intracellular or extracellular cell surface. The cargo associated with the cell penetrating peptide (forming a construct or complex or nanoparticle) may enter the cell via the endosomal pathway. The construct or complex or nanoparticle may then be encapsulated in an intra-organelle, preferably in an endosomal compartment or in a lysosome, and subsequently released into the intracellular compartment or environment.

Cargo includes peptides, proteins, non-peptidic pharmaceutical, polysaccharides, lipids, combinations thereof including lipoproteins and glycolipids, nucleic acids (e.g. DNA, siRNA, microRNA, shRNA, antisense oligonucleotides, decoy DNA, plasmid DNA), small molecule drugs, imaging agents (e.g. fluorophore), radioactive tracers, metal chelates). When the cargo molecule is a peptide, polypeptide or protein, it may comprise one or more peptides, polypeptides or proteins linked together. The peptide may be selected from a group consisting of, but not limited to, a cell or tumour targeting peptide, an aptamer, a receptor ligand, a peptide ligand, a cytotoxic peptide, a bioactive peptide, an antibody, and a diagnostic agent. When the cargo molecule is a nucleic acid, the nucleic acid may comprise one or more nucleic acids where each one encodes one peptide or polypeptide. The cargo molecule may be a combination of a protein, a lipid, and/or a polysaccharide including lipoproteins and glycolipids. The cargo may be selected from a group consisting of, but not limited to, oligonucleotides including single-stranded oligonucleotides (e.g. DNA, RNA, PNA, LNA and their analogues), double-stranded oligonucleotides (e.g. siRNA, shRNA, microRNA and decoyDNA) and cyclic DNA (e.g. plasmids).

In one embodiment of the present invention, the construct comprises a cargo covalently attached thereto.

In the case of covalent attachment, a linker moiety may optionally be present between the cell penetrating peptide and the cargo molecule, i.e. such a linker may link or connect the cell penetrating peptide and the cargo molecule together. The covalent attachment e.g. the linker moiety may be biodegradable to facilitate release of the cargo into the intracellular compartment or environment.

In a further embodiment of the present invention, a complex comprises a construct according to the present invention and a cargo non-covalently interacting therewith, for example via ionic interactions. Such cargo suitably is ionic and carries negative charges. In a specific embodiment of the present invention, the complex forms a nanoparticle. The complex self-assembles into a nanoparticle. The nanoparticle of the present invention comprises the amphiphilic cell penetrating amino acid sequence and associated cargo, the nanoparticle being intact upon entry into the cell. The nanoparticle of the present invention may for example be 20 to 60 nm in diameter, preferable 30 to 40 nm in diameter. Upon entry into the cell, the nanoparticle may undergo phase transition, for example inside endosomes/lysosomes, which provide a sufficiently low pH environment, thereby releasing the associated cargo into the cell.

In a preferred embodiment, the cargo non-covalently interacts (e.g. ionic interactions) with the construct and forms a complex. In a preferred embodiment, siRNA as cargo non-covalently interacts (e.g. ionic interactions) with the construct and forms a complex. In yet a further preferred embodiment, the complex formed of siRNA non-covalently interacting (e.g. ionically interacting) with the construct, forms a nanoparticle.

In Vitro and Ex Vivo

The constructs or complexes of the present invention may be used to transfect cells in vitro, in particular stable transfection. The constructs of complexes of the present invention may be used to transfect cells ex vivo, in particular stable transfection. The constructs or complexes may be used to deliver siRNA or pDNA into many commonly used cell types. Cells or cell lines or cell types that may be transfected include, but are not limited to, HeLa, NIH 3T3, HEK-293, CHO-K1, U2-OS, and COS-7, and several hard-to-transfect cell lines, such as Jurkat, CaCo2, a human adenocarcinoma cell lines, dendritic cells, epidermis cells.

Treatment and Prevention of Cancer or Endometriosis

The present invention provides a pharmaceutical composition for use in medicine. The present invention further provides a pharmaceutical composition for use in a method of treating or preventing cancer. The cancer may be a solid tumour. The present invention further provides a pharmaceutical composition for use in a method of treating endometriosis.

Cancer

The cancer may be any cancer or tumour that is a solid cancer or tumour. The solid cancer or tumour may be bone, bladder, brain, breast, colon, oesophagus, gastrointestinal tract, genito-urinary tract, kidney, liver, lung, nervous system, ovary, pancreas, prostate, retina, skin, stomach, testicular and/or uterus cancer. A cell penetrating peptide of the invention associated with any cargo molecule as described in the present description may be used in the treatment of cancer. The cargo molecule may inhibit tumour growth, metastasis, angiogenesis and/or resistance. The cargo molecule may target genes or proteins associated with, for example, tumour growth and angiogenesis such as VEGF.

Endometriosis

Endometriosis is a gynaecological disease described by the presence of endometrial tissue outside the uterine cavity. Endometriotic lesions are most commonly found in the peritoneal cavity, on the outer surface of the uterus, the ovaries, the bladder or attached to the peritoneum. Endometriosis may be treated by gene therapy, where specific genes that are abnormally expressed in the disease tissue are downregulated. Vascular endothelial growth factor (VEGF) is a widely known target gene in cancer therapy and is overexpressed in most endometriotic lesions. VEGF may be used as a target gene in endometriosis therapy or treatment. siRNAs may be used to silence the VEGF gene in endometriosis therapy or treatment.

Pharmaceutical Compositions

The constructs or complexes of the invention may be formulated for delivery in pharmaceutical compositions. The pharmaceutical composition will normally be sterile and will typically include a pharmaceutically acceptable carrier and/or adjuvant. A pharmaceutical composition of the present invention may additionally comprise a pharmaceutically acceptable adjuvant and/or carrier. Compositions of the invention suitably comprise a construct or complex of the invention together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. topical, oral, nasal, intravenous, intramuscular, intradermal, intracranial, intraocular, intraperitoneal, subcutaneous, spinal or other parenteral routes of administration, for example by injection or infusion. For parenteral administration, the carrier preferably comprises water and may contain buffers for pH control, stabilising agents e.g., surfactants and amino acids and tonicity modifying agents e.g., salts and sugars. If the composition is intended to be provided in lyophilised form for dilution at the point of use, the formulation may contain a lyoprotectant e.g., sugars such as trehalose. For oral administration, any of the above carriers or a solid carrier, such as mannitol, lactose, starch, magnesium stearate, sodium saccharine, talcum, cellulose, glucose, sucrose, and magnesium carbonate, may be employed. Alternatively, the carrier may be suitable for non-parenteral administration, such as a topical, epidermal or mucosal route of administration. The carrier may be suitable for oral administration. Depending on the route of administration, the modulator may be coated in a material to protect the compound from the action of acids and other natural conditions that may inactivate the compound.

Thus, compositions of the invention may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, solutes that render the formulation isotonic, hypotonic or weakly hypertonic with the blood of a recipient, suspending agents, thickening agents and/or preservatives. Alternatively, compositions of the invention may be formulated as a lyophilizate.

The pharmaceutical compositions of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

Pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be desirable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration. Pharmaceutical compositions of the invention may comprise additional active ingredients. In therapeutic applications, compounds are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is typical.

A pharmaceutical composition of the present invention may be administered via one or more routes of administration using one or more of a variety of methods known in the art. As will be appreciated by the skilled artisan, the route and/or mode of administration will vary depending upon the desired results. Examples of route of administration for compounds or pharmaceutical compositions of the invention include intravenous, intramuscular, intradermal, intraocular, intraperitoneal, subcutaneous, spinal or other parenteral routes of administration, for example by injection or infusion. The phrase "parenteral administration" as used herein mean modes of administration other than enteral and topical administration, usually by injection. Alternatively, the pharmaceutical composition of the invention can be administered via a non-parenteral route, such as topical, epidermal or mucosal route of administration. The pharmaceutical composition of the invention may be for oral administration.

A suitable dose of the pharmaceutical composition of the invention may be determined by a skilled medical practitioner. Actual dosage levels of the active ingredients in the pharmaceutical compositions of the present invention may be varied so as to obtain an amount of the active ingredient that is effective to achieve the desire therapeutic response for a particular patient, composition and mod of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dosage may be, for example, in the range of from about 0.01 ug/kg to about 1000 mg/kg body weight, typically from about 0.1 ug/kg to about 100 mg/kg body weight, of the patient being treated. For example, a suitable dosage may be from about 1 ug/kg to about 10 mg/kg body weight per day from about 10 ug/kg to about 5 mg/kg body weight per day.

Dosage regimens may be adjusted to provide the optimum desired response, for example a therapeutic response. For example, as single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contain a predetermined quantity of active compound calculated to produce the desired therapeutic effect in association with the required pharmaceutical carrier.

Administration may be in single or multiple doses. Multiple doses may be administered via the same or different routes and to the same or different location. Alternatively, doses can be via a sustained release formulation, in which case less frequent administration is required. Dosage and frequency may vary depending on the half-life of the pharmaceutical composition in the patient and the duration of treatment desired.

Pharmaceutical compositions of the present invention may be co-administered with one or more other therapeutic agents.

Combined administration of two or more agents may be achieved in a number of different ways. Both may be administered together in a single composition, or they may be administered in separate compositions as part of a combined therapy. For example, one may be administered before or separately, after or sequential, or concurrently or simultaneously with the other.

Thus, in an embodiment, there is provided a pharmaceutical composition comprising a construct or complex of the invention together with a pharmaceutically acceptable carrier.

In certain preferred embodiments of the present invention, pharmaceutical compositions of the invention are provided which comprise one or more (e.g., one) polypeptides of the invention in combination with a pharmaceutically acceptable carrier.

In certain preferred embodiments of the present invention, compositions of the invention are provided which comprise one or more (e.g., one) nucleic acids of the invention or one or more (e.g., one) vectors of the invention in combination with a pharmaceutically acceptable carrier.

In an embodiment, the compositions of the invention may comprise one or more (e.g., one) polynucleotide and one or more (e.g., one) polypeptide components. Alternatively, the compositions may comprise one or more (e.g., one) vector and one or more (e.g., one) polypeptide components. Alternatively, the compositions may comprise one or more (e.g., one) vector and one or more (e.g., one) polynucleotide components. Such compositions may provide for an enhanced immune response.

Diagnosis

Diagnosis includes determining whether or not an individual has a cancer or tumour, or endometriosis, and/or determining the severity of the cancer or tumour, or endometriosis. Prognosis includes predicting whether or not an individual will develop a cancer or tumour, or endometriosis, whether or not they will need treatment, the type of treatment the individual will need, whether or not they will respond to treatment, whether or not and/or when they will suffer a cancer or endometriosis episode, recurrence or relapse, and the severity or duration of a symptom or a cancer or endometriosis episode, recurrence or relapse. The method of prognosis may predict whether or not an individual in remission from cancer will have a recurrence. Predicting whether or not the individual will have a recurrence includes determining the likelihood that the individual will have a recurrence, and/or when they will have a recurrence.

Predicted responsiveness in an individual to a given therapy means that the individual is expected to derive benefit, or a sufficient extent of benefit, from receiving the therapy. Predicted non-responsiveness in an individual to a therapy means that the individual is not expected to derive benefit, or a sufficient extent of benefit, from receiving the therapy.

A method of diagnosing or detecting cancer in a patient may comprise administering an effective amount of the construct or complex of the present invention comprising at least one imaging agent and/or labelling molecule.

A method of diagnosis or prognosis may include selecting or recommending a suitable treatment for the individual, i.e. based on the diagnosis or prognosis. The selected or recommended treatment may then be administered to the individual.

EXAMPLES

Materials and Methods

Peptide Modelling

All peptide sequences were modelled and the charge or logD calculations were performed using MarvinSketch 15.9.14, ChemAxon Ltd, USA.

Cell Culture Maintenance

U87 MG-luc2 human glioma cells, stably expressing luc2 and U87 cells were grown on gelatinized (0.1% gelatine, Naxo, Estonia) dishes at 37° C., 5% $CO_2$ in Dulbecco's Modified Eagle's Medium (DMEM) (Sigma, Germany). CHO and CHO stably expressing green fluorescent protein (GFP) were grown at 37° C., 5% $CO_2$ in Ham's F12 nutrient mixture (Capricorn, Thermo Fisher Scientific, USA). Cell media were supplemented with 0.1 mM non-essential amino acids, 1.0 mM sodium pyruvate, 10% fetal bovine serum (FBS) (Sigma, Germany), 100 U/ml penicillin and 100 mg/ml streptomycin (Invitrogen, Sweden).

Solid Phase Peptide Synthesis

Peptides were synthesized on an automated peptide synthesizer (Biotage Initiator$^+$ Alstra) using fluorenylmethyloxycarbonyl (Fmoc) solid phase peptide synthesis strategy with Rink-amide ChemMatrix resin (0.45 mmol/g loading) to obtain C-terminally amidated peptides. The fatty acid was coupled manually to the N-terminus of the peptide overnight, at room temperature with 5 eq. fatty acid. For the synthesis of ornithine containing peptides Boc-L-Orn (Fmoc)-OH (Iris Biotech, Germany) was used. Reaction was carried out using HOBT/HBTU as coupling reagents in DMF with DIEA as an activator base. For the synthesis of PF6, chloroquine analogs (trifluoromethyl quinoline derivative) were coupled to the lysine tree over succinic anhydride (Sigma-Aldrich) added to the Lys7 (with Mtt sidechain protecting group removed with 0.1% TFA and 3% TIS in DCM. Fmoc-Lys (Fmoc) (Iris Biotech)) of the peptide.

Cleavage was performed with trifluoroacetic acid, 2.5% triisopropylsilane and 2.5% water for 2 h at room temperature. Peptides were purified by reversed-phase high-performance liquid chromatography on C4 column (Phenomenex Jupiter C4, 5 μm, 300 Å, 250×10 mm) using a gradient of acetonitrile/water containing 0.1% TFA. The molecular weight of the peptides was analyzed by matrix-assisted laser desorption-ionization/time of flight mass spectrometry (Brucker Microflex LT/SH, USA). Concentration of the peptides was determined based on dilutions of accurately weighed substances and absorption of tyrosine, where applicable.

Peptide Environment pH Maintenance Assay by Titration

To assess the ability of peptides to maintain the pH of the solution in a certain range (due to the histidines added to the sequence) we prepared 5 ml of a 200 uM peptide solution in mQ water and added 1 M TFA to achieve the same pH 2.5 for all peptide solutions. We added 0.5 M NaOH (5 ul) solution while stirring and measuring pH after each step. The change in pH was documented and titration curve is shown as a graph (pH vs added NaOH solution).

The formation of peptide/siRNA complexes and experiments on cells: downregulation of the reporter gene, pDNA and splice correcting oligo (SCO) transfection, fluorescence-assisted cell sorting (FACS), and confocal microscopy For assessing the siRNA mediated RNAi, CHO-GFP or U87-luc2 cells ($5\times10^5$ cells per well) were seeded on a 24-well plate a day prior to the experiment and grown in serum containing media. On experiment day, prior to adding pre-formed complexes (1/10th of the final volume per well), media was replaced with fresh serum containing medium.

For complex formation, peptide was mixed with luc2 siRNA (sense 5'-GGACGAGGACGAGCACUUCTT-3' (SEQ ID NO:7), antisense 5'-GAAGUGCUCGUCCUCGUCCUU 3' (SEQ ID NO:8), Metabion, Germany) or with siRNA against GFP (5'-GGCUACGUCCAG-GAGCGCACC (SEQ ID NO:9), 3'-UGCGCUC-CUGGACGUAGCCUU (SEQ ID NO:10)) in mQ water (pH 5.3-6.3) using peptide to siRNA molar ratios (MR is the ratio of peptide to siRNA) 40:1 and incubated at RT for 1 h. For siLuc2, the final concentration in media was 25 nM and for siGFP 100 nM. Cells were co-incubated with complexes for 4 h (37° C., 5% $CO_2$), thereafter fresh serum containing media was added and followed by further incubation (20 h for siLuc2 or 44 h for siGFP complexes). Luciferase gene downregulation was measured from cell lysates with Promega luciferase assay system (Promega, Sweden) in combination with GLOMAX 96 microplate luminometer equipped with GLOMAX 1.9.2 software (Promega). GFP was measured after treatment from cell lysates on black 96-well plates by measuring total fluorescence (Symergy MX, BioTek Instruments, USA equipped with Gen5 1.10 software). The results were normalized to the protein content of each sample (DC Protein Assay, BioRad, USA).

For the pDNA transfection experiment, CPP/pDNA nanoparticles were prepared by mixing 0.5 mg of plasmid (p-CMV-Luc2) with the peptide in MQ water. Charge ratios from 1 to 4 (CR, equivalent to the nitrogen-to-phosphate ratio) were used. 50,000 CHO cells were seeded 24 hr before the experiment into 24-well plates, treated with complexes for 4 h in serum-containing medium, incubated for additional 20 hr, lysed and luminescence was measured.

For determination of IC50, complexes were formed at MR30 and diluted before addition on cells to the final siRNA concentrations 100, 50, 25, 12.5, 6.25, 3.13, 1.6, 0.7 and 0.3 nM in wells. Luciferase activity was determined as described in previous paragraph.

For determination of pH dependency on the transfection efficiency, complexes were formed at MR30, incubated and diluted before addition to cells to obtain siRNA final concentration 10 nM in transfection media. HEPES buffer supplemented with 10% FBS was used as transfection media. Complexes were co-incubated with cells for 4 h and then media was replaced with cell growth media. After further 20 h incubation cells were lysed and analyzed as described previously.

For flow cytometry analysis (FACS) analysis CHO-GFP cells were seeded and treated as described previously. After incubation, cells were washed with 1× PBS and detached from plates with trypsin-EDTA (0.25%), and re-suspended in PBS supplemented with FBS (5%) and transferred to transparent U-bottom 96-well plates. FACS was carried out with BD LSR II flow cytometer (BD Biosciences, San Jose, CA, USA) equipped with a 488 nm argon laser. Population of viable cells was determined from scatter plot: forward scattered plot (FSC) vs. side scattered light (SSC) plot. A minimum of 10,000 events from the viable cell population per sample were analyzed using BD FACS Diva software. Results are shown as the population with GFP signal lower than that of 0.1% of untreated cells.

For confocal microscopy $2\times10^5$ cells per chamber were seeded on NUNC 8-chamber plates. After treatment with complexes (25 ul of pre-formed CPP/siRNA complexes added to cells in 225 ul serum containing media), incubated (48 h) and GFP florescence images of cells were captured using confocal microscope Zeiss LSM 710 and excitation at 488 nm (493-616 filter).

Negative Staining and Visualisation of Complexes by TEM

For the morphological analysis the CPP/siRNA complexes were assembled as described above at MR30. For negative staining, copper grids were covered with Formvar film and carbon layer using Leica EM ACE600 carbon coater (Leica Microsystems, Germany). Then, 10 μL of each sample was absorbed to the grids for 2 min and excess of solution was gently removed. Samples were then exposed to 2% aqueous uranyl acetate solution for 1 min. After removing excess stain with filter paper, the samples were allowed to air-dry. The samples were examined at 120 kV accelerating voltage on FEI Tecnai G2 Spirit electron microscope (FEI, The Netherlands).

Dynamic Light Scattering (DLS) and Zeta-Potential Measurements

Hydrodynamic mean diameter of the nanocomplexes was determined by dynamic light scattering studies using a Zetasizer Nano ZS apparatus (Malvern Instruments, UK). Peptide/siRNA complexes were prepared in mQ water as described for transfection. All results were based on three measurements from four independent samples. All data were converted to "relative by intensity" plots from where the mean hydrodynamic diameter was derived.

Membrane Activity Assay on Murine Red Blood Cells: Hemolysis

For evaluation of membrane activity of peptides, hemolysis assay was used. For this whole blood was collected from mouse (adult, BALB/c) saphenous vein into a heparinized collection tube. Blood was centrifuged (2300× g, 15 min) to separate cells (red blood cells-RBC) from the plasma. RBCs were washed according to following procedures.

RBCs were washed with 10 ml 0.9% NaCl saline and centrifuged (600× g, 15 min). Supernatant was discarded after each centrifugation. This was repeated at least 3 times. RBCs were re-suspended in 5 ml saline and distributed equally to tubes and centrifuged (600× g, 15 min). The cells were washed and re-suspended in 2× PBS with the required pH (pH 5.5-7.5). The hemoglobin content in stocks was measured after lysis of cells with equal volume of 0.1% Triton X100 supplemented with 5% glucose. The cell suspension was diluted accordingly for each pH value to obtain similar concentration range of hemoglobin in stocks. To each 100 ul of peptide solution 100 ul of 10% glucose was added, mixed, and equal volume (200 ul) of RBC in 2× PBS were added and gently mixed. Peptide solution with RBCs was incubated at 37° C. for 1 h with gentle mixing (max 300 rpm) after which samples were centrifuged to pellet intact cells from the solution. Hemoglobin from lysed cells was determined from each sample from the supernatant on transparent 96-well plates by measuring the absorbance at 540 nm.

Controls were incubated in similar manner as samples. As a non-hemolysis control mQ supplemented with glucose (0%) was used and for hemolytic control 0.1% TritonX-100 with glucose (100%) was used (cells are suspended in 2× PBS before addition). Final percent was calculated as follows:

$$\text{Hemolysis} = 100 * \frac{A(\text{sample}) - A(0\%)}{A(100) - A(0\%)}$$

For hemolytic concentration determination 2× PBS at pH 7.5 was used for incubation and 1× PBS at pH 7.5 was used for washing. Everything else is as described in previous paragraph.

MTS Toxicity Assay

Cell proliferation was determined with the CellTiter 96® Aqueous Non-Radioactive Cell Proliferation Assay (MTS) (Promega Biotech AB, Sweden) according to the manufacturer's instructions. For this 1×10$^5$ U87 cells were seeded 1 day prior to experiment on transparent 96-well plates. On experiment day, media was replaced with 90 ul of fresh media and to the cells complexes formed at MR30 (both with 25 nM and 100 nM final siRNA concentrations) or free peptide at the range of 0.5-4 uM final concentrations were added. Cells were treated with complexes for 20 h. MTS was added according to the manufacturer's protocol. The absorbance of formazan product was measured at 490 nm with Tecan Sunrise microplate absorbance reader (Tecan Group Ltd, Switzerland) and percentage of viable cells was calculated using GraphPad Prism software 5.0 (Graphpad Software, CA, USA).

Fluorescent Dye Intercalation Assay

Complexation of siRNA and CPPs was assessed by Quant-iT™ PicoGreen® (PG) (Thermo Fisher Scientific, USA) assay in mQ water. Complexes were prepared as described previously, following addition of diluted PG. For detection, complexes (⅕ of volume), water (3/5) and PG (1/5) working dilution was incubated for 5 minutes and fluorescence was measured by fluorimeter ($\lambda_{ex}$=492 nm, $\lambda_{em}$=535 nm) (SynergyMx, BioTek). For heparin displacement, instead of water, heparin salt solution at different concentrations were used and complexes incubated at 37° C. for 30 min before addition of PG dilution. Complex formation was also confirmed by gel electrophoresis (details in section 2.11).

To assess protection of siRNA from enzymatic degradation, after addition of PG dilution and initial measurement to set a starting point, Proteinase K (Thermo Scientific, USA) was added (>14 U/ml, 20 ul of mixture per well containing dilution of 120 ul of enzyme in 1 ml), co-incubated with complexes and fluorescence was measured over a 10 h period.

Stability of Complexes to Serum

The stability of CPP/siRNA complexes was assessed by adding 50% of FBS to complexes and further incubating at 37° C. for 1-24 h. After 1, 3, 6 and 24 h samples for analysis were collected. As a control for total siRNA remaining in complexes FBS incubated complexes were treated with Triton X100 and heparin sodium salt (final concentrations 0.1% and 3.33 mg/ml respectively) for 10 minutes prior to transferring them to the agarose gel. All samples were mixed with RNA loading buffer and transferred to 1.8% agarose gel in 1× TAE buffer, electrophoresed, and visualized by ethidium bromide (5 ug) (Sigma, Sweden). Bands were imaged under UV light.

Gene Downregulation In Vivo

For the gene downregulation studies male Balb/c, 2-4 month-old mice were used, with 2-5 mice per group. The CPP/siRNA complexes were formed at MR30 and for each mouse 1.6 mg/kg siRNA dose was used. Particle formulations were administered intravenously via tail vein injection, at 1.6 mg/kg siRNA dose. 48 h post treatment, liver tissues were harvested and snap-frozen for analyses. The tissues were homogenized using Precellys®24-Dual homogenization system (Bertin Technologies, France) with TRIzol reagent (Thermo Fisher Scientific). RNA was extracted according to TRIzol manufacturers protocol with slight modifications. RNA quality and concentration was assessed on 1.8% agarose gel and NanoDrop2000. From RNA complementary DNA was synthesized using SuperScript IV Reverse Transcriptase (Thermo Fisher Scientific) according to manufacturer's protocol. The synthesized cDNA was used for qPCR accompanied with 5× HOT FIREPol EvaGreen qPCR Supermix (Solis Biodyne, Estonia) according to manufacturer's protocol. The obtained data was analyzed using 2-ΔΔCT method and normalized to untreated mouse group (100%). siRNA against blood coagulation factor VII (siFVII) sense 5'-gga (2'F-U) (2'F-C) a (2'F-U) (2'F-C) (2'F-U) (2'F-C) aag (2'F-U) (2'F-C) (2'F-U) (2'F-U) a (2'F-C) T*T-3" and antisense 5'-g (2'F-U) aaga (2'F-C) (2'F-U) (2'F-U) gaga (2'F-U) ga (2'F-U) (2'F-C) (2'F-C) T*T 3'. Primers for PCR (Mus blood coagulation factor VII) forward ACAAGTCTTACGTCTGCTTCT (SEQ ID NO:11), reverse: CACAGATCAGCTGCTCATTCT (SEQ ID NO:12) and (Mus Actin beta) forward: CCACACCCGC-CACCAGTTCG (SEQ ID NO: 13) and reverse: TACAGCCCGGGGAGCATCGT (SEQ ID NO:14). The siRNA and primers were synthesized by the same manufacturer (Metabion, Germany). Data was collected with ViiA 7 RT_PCR system and analysis based on 2-4ΔCT and normalized to results from untreated mice.

As a control hydrodynamic injection of 600 ul of siRNA was used and untreated mice were included. All animal experiments and procedures were approved by the Estonian Laboratory Animal Ethics Committee (approvals no 81, dated Apr. 4, 2016, and 69 and 70, dated Feb. 9, 2011).

Gene Delivery In Vivo

For in vivo pDNA delivery studies BALB/c mice were used. Each animal received a single 200 mL intravenous (i.v.) injection of the complexes at CR2 or CR4. Two doses of pDNA 20 mg and 50 mg were used. After 24 hr, the mice were sacrificed using cervical dislocation, and whole organs were harvested and snap-frozen on dry ice. The organs were homogenized, and luminescence was measured.

Biodistribution of CPP/Cy5-Labeled siRNA Nanoparticles In Vivo

Human tumor xenografts (subcutaneous U87MG and HT-1080) were induced in mice (Hsd: Athymic Nude-Foxn1nu female, 2.5 month old, Harlan, UK). The xenografting was performed by implanting the cell suspension (1×10$^6$ cells in 100 ul volume of ice-cold DMEM without any supplements) subcutaneously to the flank.

At the appearance of tumor size of approx. 100 mm$^3$, mice were injected i.v. (via tail vein) with the CPP/siRNA complexes. Each animal received a single 200 ul i.v. injection of 20 ug Cy5-siRNA, formulated with CPPs at MR20 or MR40. As a control, 20 μg of un-complexed Cy5-labeled siRNA was administered. The biodistribution of Cy5-siRNA and CPP/Cy5-siRNA complexes was evaluated at different time points –0.5 h up to 6 h. For that, mice (n=2 in each treatment group) were imaged in vivo using IVIS Lumina II (CaliperLS, USA). Cy-5 fluorescence intensity values were acquired from the tumor region.

Statistical Analysis

Statistical analysis of cell culture, fluorescent label intercalation assay and in vivo experiments were done on GraphPad Prism software 5.0 (Graphpad Software, CA, USA). All results are shown as a mean with SEM of at least three separate experiments, if not indicated otherwise.

The constructs and complexes referred to in the Examples and in the Figures may be interpreted with reference to Table 1.

Example 1

Figure 2:
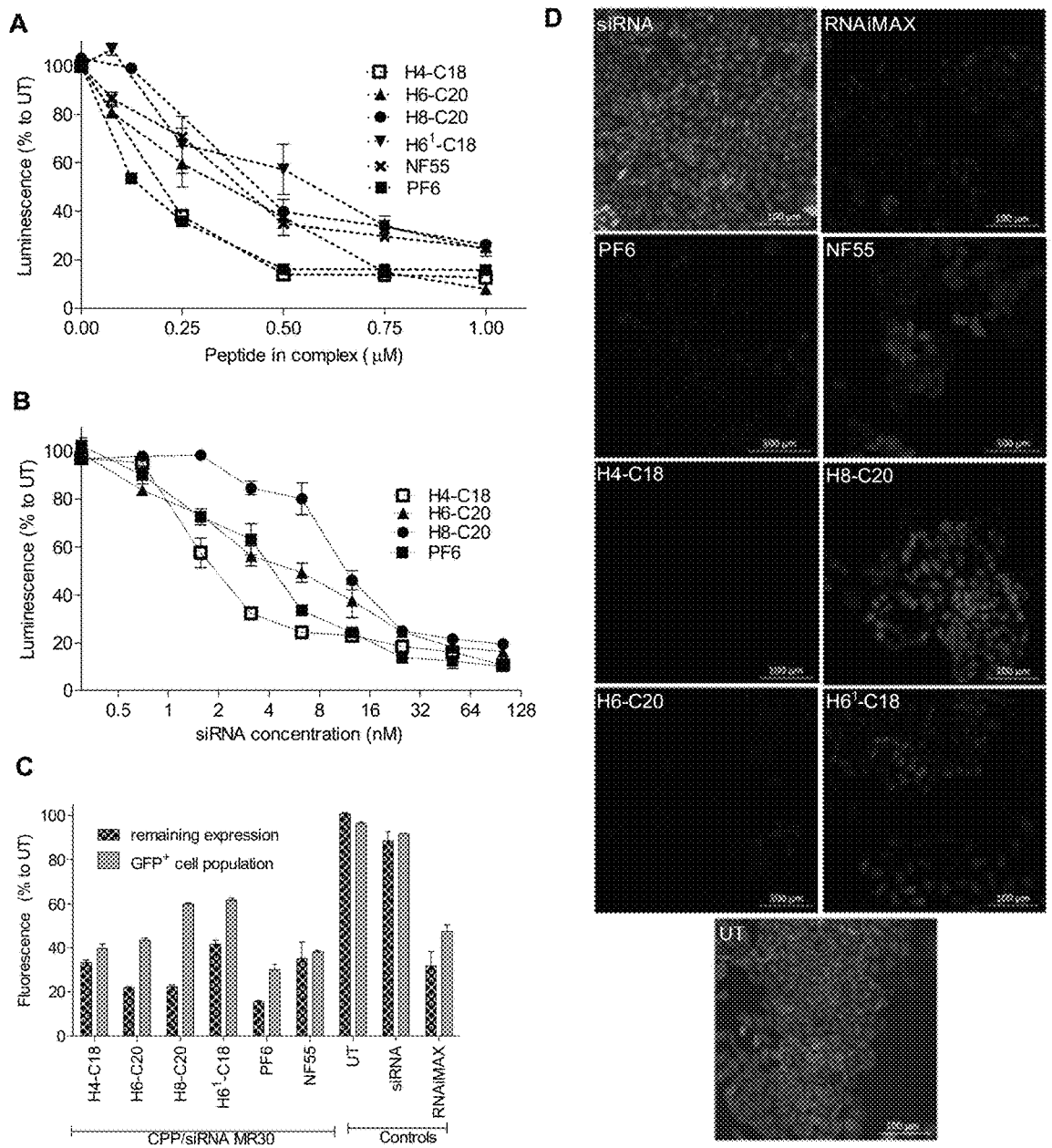
FIG. 2 shows the bioactivity of delivered siRNA and percentage of cell population transfected by CPP/siRNA complexes. Results are normalised to protein content and untreated cells (100%). A) Luminescence from reaction with expressed luciferase, measured at 24 h post-transfection with complexes containing different concentrations of CPP and siRNA final concentration 25 nM; B) Luminescence from reaction with expressed luciferase after treatment with CPP/siRNA complexes formed at MR30 (MR30, ratio of peptide to siRNA) and siRNA final concentration ranging from 0-100 nM; C) Downregulation of GFP gene expression. Fluorescence measured from whole cell lysate (remaining fluorescence compared to untreated cells) and FACS analysis (GFP$^+$ cell population) of cells treated with siGFP or CPP/siRNA complexes; D) Confocal microscopy images of live cells treated with CPP/siGFP complexes.
Figure 13:
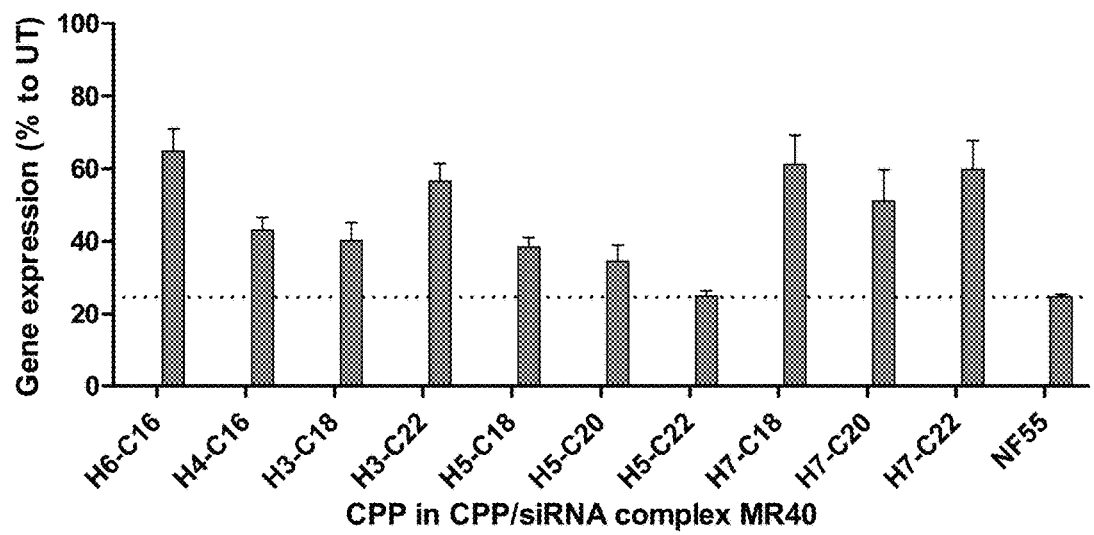
FIG. 13 shows the remaining gene activity after transfection with CPP/siRNA complexes containing siRNA against luciferase. Results are normalised to protein content and untreated cells (100%). Novel CPPs were tested.

Histidine containing CPP/siRNA complexes led to a downregulation of the target gene expression in the cells Most of the histidine-containing CPP complexes with siRNA were active at tested conditions (FIGS. 1 and 13). From all series with different fatty acid (Table 1, FIGS. 1 and 13) we chose the CPPs that in complex yielded the highest degree of downregulation of reporter gene in the cells and continued with the characterization of CPP/siRNA complex properties (FIGS. 2A and 2C). siRNA downregulation in the H6² series was significantly lower compared to the other peptides (FIG. 1). In H6² series the remaining reporter activity was approximately 40% at molar ratio 30 (MR30, ratio of peptide to siRNA), whereas with H4-C18, H6-C20, H6¹-C18 and H8-C20 it had dropped to 13%, 15%, 19% and 34% respectively (FIG. 1 and FIG. 2A).

TABLE 1

The CPPs used in Examples 1-9, their calculated charge and neutrality condition. All peptides are C-terminally amidated.

| $C^a$ | CPP | $FA^b$ | $Red^g$ (%) | Peptide sequence | Charge$^c$/NC$^d$ pH 7.4 | Charge$^c$/NC$^d$ pH 6.0 | LogD$^c$ pH 7.4 | LogD$^c$ pH 6.0 |
|---|---|---|---|---|---|---|---|---|
| — | NF55* | 18 | 75 | AGYLLGO$^e$INLKALAALAKAIL | 3.1/14 | 3.8/11 | 0.4 | -2 |
| — | PF6* | 18 | 84 | AGYLLGK$^f$INLKALAALAKKIL | 8.9/5 | 10.9/4 | nd | nd |
| H3 | NF725 | 18 | 60 | HYHHGO$^e$ILLKALKALAKAIL | 4.3/10 | 7.1/6 | -3.2 | -8 |
|  | NF726 | 20 | 50 |  |  |  | -2.1 | -7 |
|  | NF727 | 22 | 43 |  |  |  | -1.1 | -6 |
| H4 | NF717 | 16 | 43 | HHYHHGO$^e$ILLKALKALAKAIL | 4.6/9 | 7.8/5 | -4.6 | -9 |
|  | NF71 | 18 | 88 |  |  |  | -3.6 | -8 |
|  | NF712 | 20 | 83 |  |  |  | -2.5 | -7 |
|  | NF713 | 22 | 47 |  |  |  | -1.5 | -6 |
| H5 | NF715 | 18 | 62 | HHHYHHGO$^e$ILLKALKALAKAIL | 5.0/8 | 8.6/5 | -4.6 | -9 |
|  | NF716 | 20 | 65 |  |  |  | -3.5 | -8 |
|  | NF718 | 22 | 75 |  |  |  | -2.5 | -7 |
| H6 | NF700 | 0 | 6 | HHHHYHHGO$^e$ILLKALKALAKAIL | 5.2/8 | 9.3/5 | 12.6 | 17.5 |
|  | NF701 | 10 | 20 |  |  |  | -8.6 | -14 |
|  | NF711 | 16 | 35 |  |  |  | -6.5 | -11 |
|  | NF702 | 18 | 70 |  |  |  | -5.5 | -10 |
|  | NF70 | 20 | 92 |  |  |  | -4.5 | -9 |
|  | NF703 | 22 | 73 |  |  |  | -3.5 | -8 |
| H6¹ | NF704 | 18 | 82 | HHHHHGO$^e$ILLKALKALAKAIL | 5.3/8 | 9.4/4 | nd |  |
|  | NF705 | 20 | 52 |  |  |  |  |  |
|  | NF706 | 22 | 59 |  |  |  |  |  |
| H6² | NF707 | 18 | 70 | HHHHHHYLGO$^e$ILLKALKALAKAIL | 5.1/8 | 9.0/5 |  |  |
|  | NF708 | 20 | 71 |  |  |  |  |  |
|  | NF709 | 22 | 55 |  |  |  |  |  |
| H7 | NF719 | 18 | 39 | HHHHHYHHGO$^e$ILLKALKALAKAIL | 5.6/8 | 10.1/4 | -6.5 | -10 |
|  | NF723 | 20 | 49 |  |  |  | -5.5 | -9 |
|  | NF724 | 22 | 40 |  |  |  | -4.5 | -8 |
| H8 | NF721 | 18 | 55 | HHHHHHYHHGO$^e$ILLKALKALAKAIL | 5.9/7 | 10.8/4 | -7.5 | -11 |
|  | NF72 | 20 | 80 |  |  |  | -6.5 | -10 |
|  | NF722 | 22 | 45 |  |  |  | -5.5 | -9 |

*reference (prior art) sequence
Red = reduction.
$^a$compound group based on peptide sequence.
$^b$the length of the saturated fatty acid added to the N-terminus of the peptide sequence (0—w/o fatty acid; 10—decanoyl; 18—stearoyl; 20—arachidyl; 22—behaoyl).
$^c$calculated with MarvinSketch, Chemaxon;
$NC^d$ - neutrality condition at which the theoretical positive net charge of peptides equals to the negative charges from siRNA when taking into account the calculated charge at given pH, peptides per siRNA.
$^e$peptide synthesis continued from the sidechain amino group instead of α-amino group,
$^f$lysine tree (consisting of three lysines added to the Lys7 of the peptide; the primary and side chain amino groups of the first added lysine are used to couple the second and third added lysines),
$^g$based on remaining luminescence on U87 cells post-treatment.,
nd—not determined,
H6¹—peptide with H6 sequence without Y5.
H6²—peptide with H6 sequence with histidines before tyrosine.

Figure 3:
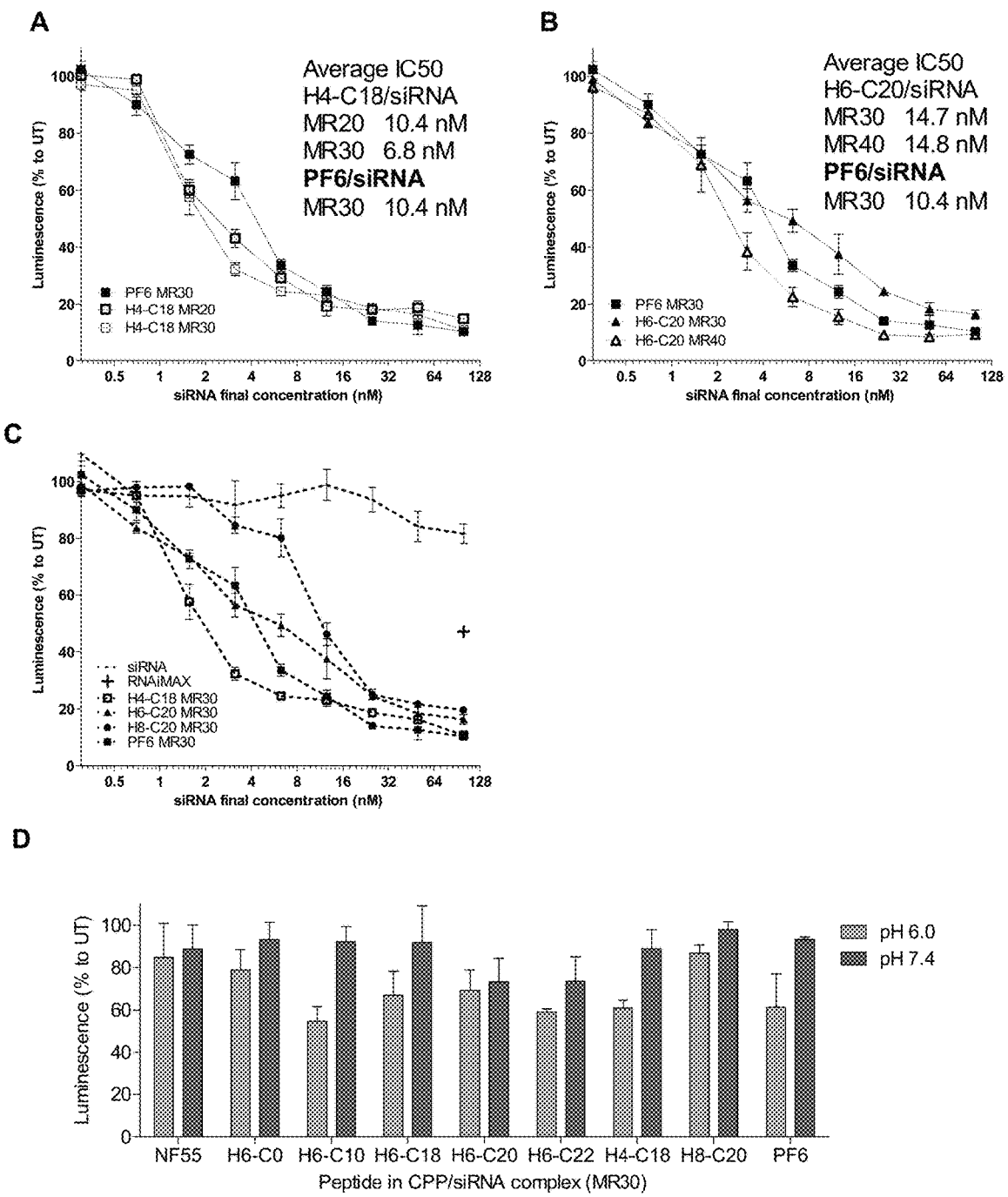
FIG. 3 shows the downregulation of the luciferase gene depending on the siRNA concentration or buffer pH. Luminescence measured from reaction with expressed luciferase after transfection by CPP/siRNA complexes; A) CPP/siRNA complexes formed with H4-C18 (NF71); B) CPP/siRNA complexes formed with H6-C20 (NF70); C) Comparison of CPP/siRNA complexes; D) Gene downregulation after transfection of cells with CPP/siRNA complexes in HEPES buffer at pH 6.0 or 7.4 and siRNA final concentration 10 nM.

In luciferase downregulation experiments, the most efficient peptides even at low MRs were H4-C18 and control peptide PF6. At MR30, H6-C20 was able to induce equally strong downregulation of the luciferase gene and at MR40 it was even more efficient than PF6 or H4-C18. Even though H6¹ and H6² series were less efficient, they still exceeded the activity of NF55 on which the peptide sequences were based (FIG. 1 and FIG. 2A). The IC50 values were lowest for complexes formed with H4-C18 with the average of 6.8 nM siRNA concentration. The IC50 values for PF6/siRNA were 1.5 times higher, with the average of 10.4 nM. For H6-C20 the values were 2.2 times higher, than for H4-C18, with the average of 14.7 nM (calculations based in results shown on FIG. 2B). The comparison of downregulation efficiency showed that higher molar ratio would lead to a lower IC50 value. In case of H6-C20, the IC50 values between complexes formed at MR30 and MR40 had similar average value of 14.7-14.8 nM (FIG. 3B), whereas the use of MR20 and MR30 in case of H4-C18 showed a decrease from 11.1 nM to 6.8 nM when MR was increased (FIG. 3A). When comparing all CPPs at MR30 the most efficient peptide was H4-C18, followed by PF6 and H6-C20. H8-C20 was significantly less efficient than other compared CPPs (FIG. 3C). The lower pH, pH 6.0, during transfection led to an increase of gene expression suppression, compared to transfection at pH 7.4, indicating a pH-dependent efficiency (FIG. 3D).

For GFP gene expression downregulation we used CHO cells stably expressing GFP and siRNA against GFP. The average downregulation of GFP was highest for CPP/siRNA complexes formed with PF6. The downregulation mediated by complexes formed with H4-C18 was lower than with H6$^1$-C20 or H8-C20. Similarly to luciferase gene downregulation, the H6 analogues H6$^1$-C18 and H6$^1$-C20 showed lower efficiency than H6-C20 (FIG. 2C). The downregulation was measured as an average for the cell lysate. We wanted to determine the fraction of the cell population that was transfected. For this we used confocal imaging and FACS on transfected cells. In confocal images, the detected GFP signal was the lowest in cells treated with H4-C18/siRNA, H6-C20/siRNA and PF6/siRNA complexes (FIG. 2D). The cells treated with H6$^1$-C18/siRNA and NF55/siRNA had similar downregulation as RNAiMAX treated cells, and H8-C20/siRNA cells exhibited higher GFP signal when compared to complexes formed with peptides with less histidines in sequence, H4-C18 and H6-C20 (FIG. 2C). FACS analysis revealed that the PF6/siRNA complexes were able to transfect and lead to the downregulation of the reporter gene in approximately 70% of the CHO cells. NF55, H4-C18 and H6-C20 had lower transfection, leading to a total of 55-60% downregulation in the cells. H6$^1$-C18 and H8-C20 had the lowest GFP cell population, with only 40% (FIG. 2C) of cell with GFP signal below given threshold.

Example 2

Figure 6:
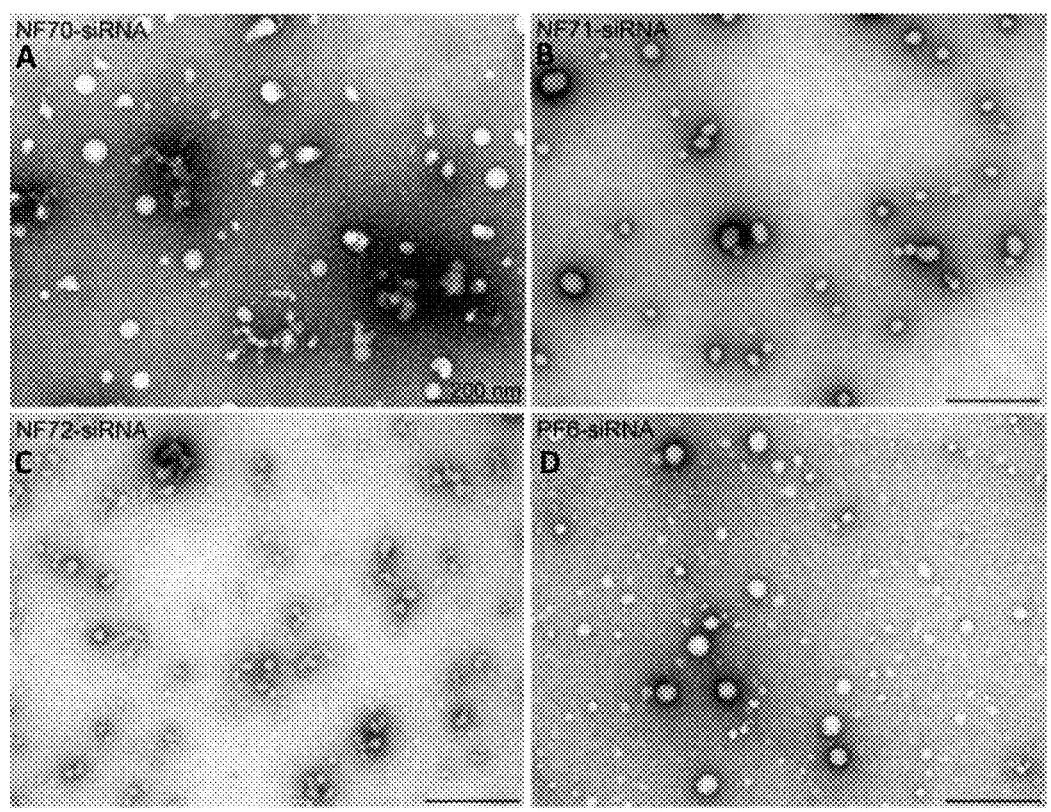
FIG. 6 shows negative staining transmission electron microscopy (TEM) images of CPP/siRNA nanoparticles formed with siRNA and A) H6-C20 (NF70); B) H4-C18 (NF71); C) H8-C20 (NF72); or D) PF6.

Histidine containing CPPs form complexes with siRNA that assemble to nanoparticles In order to characterize the nanoparticle-forming potential of H6-series (NF70-series) transfection, we assessed the morphology of the peptide complexes with siRNA using negative staining transmission electron microscopy (TEM). All H6 peptides that yielded strong downregulation of targeted luciferase by siLuc (FIG. 2) condensed siRNA to regular and homogeneous nanoparticles (FIG. 6). Remarkably, H6-C20 (NF70) that led to the strongest suppression of marker gene, formed with siRNA mostly spherical nanoparticle with 30-40 nm diameter that were highly similar to particles obtained with PF6 (FIG. 6A, D). Still a fraction of NF70-siRNA complexes had an elongated (40-80 nm) shape. H4-C18 (NF71) condensed siRNA to rather similar particles with NF70; however, their complexes were slightly less regular/spherical and homogeneous ranging from about 20 to 60 nm in diameter. This may imply that CPPs in CPP/siRNA complexes having shorter-chain fatty acids and less histidine residues have a lower condensing capacity compared to longer-chain fatty acids and more histidine residues, for example NF70.

The type of fatty acid (FA) introduced to the N-terminus of this type of CPP is one of the key determinants of the intracellular activity of delivered siRNA molecules. In the absence of fatty acid modification (NF700), the nanoparticles do not reveal any significant luciferase silencing activity (FIG. 1). Upon increasing the length of fatty acid on the peptide N-terminus, the acquired siRNA effect increases up to 95% downregulation of luciferase activity in the case of NF70 that carries C20 FA. After exceeding the optimal FA length, the RNA interference effect decreases again as observed with NF703 nanocomplexes. TEM analysis corroborates good correlation of activity with the morphology of respective nanoparticle. The FA-free NF700 forms very few stable particles with siRNA that can be detected by TEM. The observed particles are elongated and exceed 500 nm in length, and seem to be loosely packed as suggested by the high diameter of complexes (FIG. 7A). Addition of C10 or C18 FA to peptide (NF701 and NF702, respectively) substantially increases the number of forming stable nanoparticle. Furthermore, these are remarkably shorter/smaller (200-400 nm) and have lower diameter (15-20 nm) suggesting tighter packing and higher stability of nanoparticles (FIG. 7B, C) that is in very good concordance with their biological effect (FIG. 1). NF703 that contains C22 FA packs siRNA mostly to very small particles that may associate to form larger conglomerates of 10-20 nm (FIG. 7D). Analogous small nanoparticles and their conglomerates also form upon condensation of siRNA with NF72 (FIG. 6C). Although the FA in this peptide has the same length as in the most efficient peptide of this series, NF70, the forming particles are remarkably different implying that two additional histidine residues in the former might add to N-terminal of peptide more hydrophobicity than required for optimal siRNA delivery.

The predecessor on NF70s series peptides, NF55, that is very efficient cellular delivery vehicle for pDNA, mostly forms with siRNA spherical nanoparticle with varying size of 10-50 nm and also elongated conglomerates of up to 100 nm length (FIG. 7E). A commonly in vivo used transfection reagent JetPEI formed with siRNA large amorphous aggregates of hazy cords with size ranging from 200 nm to 1 µm or more (FIG. 7F).

The association of NF-siRNA nanoparticle morphology with their gene silencing effect suggests that more homogeneous particles of about 30-50 nm size enable the most efficient downregulation of target gene, and too small and too large nanoparticle, or highly heterogeneous ones lead to moderate or poor siRNA effect in cell culture conditions. Particles formed with highly cationic peptides typically lead to the formation of positively charged particles.

Example 3

Figure 4:
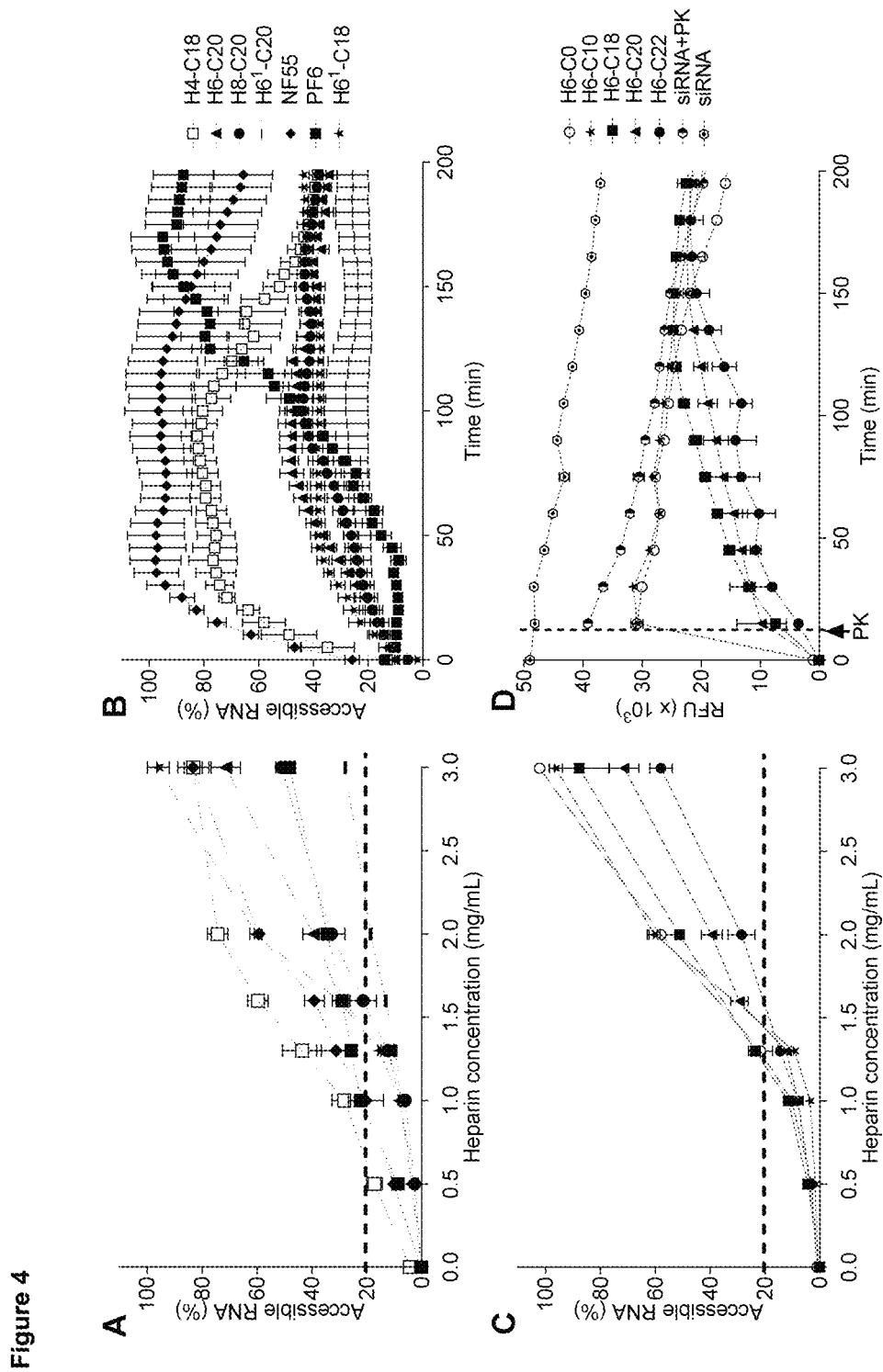
FIG. 4 shows the stability and packing of CPP/siRNA complexes; A) Heparin displacement assay of CPP/siRNA complexes pre-formed at MR30; B) Stability of CPP/siRNA complexes to degradation by Proteinase K (>14.4 U per well) measured as binding of fluorescent dye PG to nucleic acid; C) Heparin displacement in CPP/siRNA complexes formed with H6 series CPPs with different fatty acid length, normalized to free siRNA; D) Stability of CPP/siRNA complexes to degradation by Proteinase K. CPP/siRNA complexes formed with H6 series CPPs with different fatty acid lengths.
Figure 7:
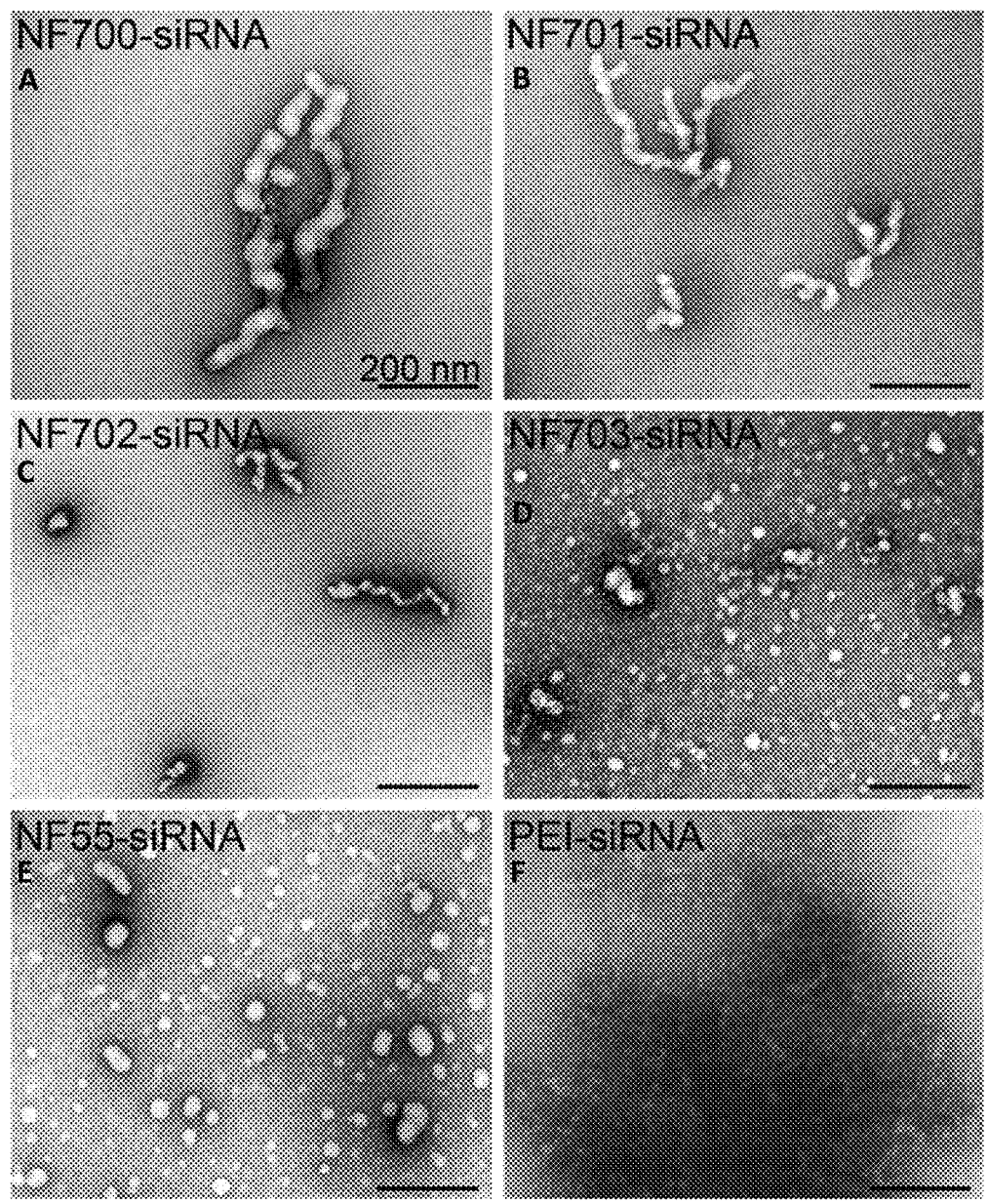
FIG. 7 shows negative staining transmission electron microscopy (TEM) images of CPP/siRNA nanoparticles formed with siRNA and CPPs from H6 series or NF55. A) NF700; B) NF701; C): NF702; D) NF703; E) NF55; F) PEI.

Histidine containing CPPs form complexes with siRNA more stable than complexes with unmodified CPP The designed peptides NF71 (H4-C18), NF70 (H6-C20), NF72 (H8-C20), H6$^1$-C18 and H6$^1$-C20 formed non-covalent complexes with siRNA as was indicated by low accessibility of siRNA at MR30 estimated by low binding of fluorescent dye to nucleic acid in intercalation assay (FIG. 4A) and TEM images (FIG. 6 and FIG. 7). Although all tested peptides formed CPP/siRNA complexes, they exhibited different stability in the presence of heparin. Heparin as a highly anionic compound is commonly used to assess the stability of interactions between siRNA and CPP in the pre-formed complexes since heparin could displace siRNA (at least partially) from the complex. NF71/siRNA complexes were less resistant to heparin displacement than NF55/siRNA (FIG. 4A) and already at 0.5 mg/ml heparin concentration 17% of siRNA was accessible compared to 10% in NF55/siRNA complex samples. NF55/siRNA and PF6/siRNA complexes had similar stability up to heparin concentration 1.3 mg/ml. At heparin concentration 2.0 and even 3.0 mg/ml the accessibility of siRNA in PF6/siRNA complexes was only about a half of that in NF55/siRNA complexes. The stability of the complexes containing NF71, NF70 and NF72 showed an increase of stability depending on the number histidines included in the peptide sequence (FIG. 4A).

What is more, the complexes formed with H6$^1$-C20 lacking the tyrosine in N-terminal peptide part (Table 1) had significantly higher stability to heparin displacement than NF70 peptide and even NF72 peptide. H6$^1$-C18, which had a higher final downregulation mediated by the delivered siRNA (FIG. 1) was not as resistant to heparin displacement as H6$^1$-C20. This could be indicating that for higher bioactivity from the siRNA an optimal siRNA and CPP interaction is needed, because in order to have biological effect, siRNA has to be released from the complexes at the target site.

When comparing the H6 peptide series with different fatty acid modifications, there was a correlation between the stability of the complex and the fatty acid length. Longer fatty acid helped to pack the complex more efficiently and lead to a higher stability in heparin displacement assay (FIG. 4C) and to enzymatic degradation (FIG. 4D). Peptide analogue with C22 was the most resistant to heparin, and even 3 mg/ml heparin concentration resulted in an only 60% of siRNA displacement (FIG. 4C).

We applied proteolytic degradation assay to assess the resistance of the pre-formed complexes to the enzymatic degradation. All complexes formed with histidine containing peptides exhibited an increase of stability to enzymatic degradation and packing ability depending on the number of His in their sequences. We used >2.4 U of enzyme per well, but the dissociation of the complexes was not sufficient even after 16 h. Therefore we increased the enzyme concentration stepwise and found that for assessing the differences of H-peptides, six times higher concentration (>14.4 U) could be used. Interestingly, the complexes with PF6 had a significantly lower stability to longer exposure to enzyme (FIG. 4B), than complexes containing NF70 and NF72 peptides. The NF71/siRNA complexes were only slightly more resistant than NF55/siRNA complexes to proteinase K. Although NF70 and H6$^1$-C20 have the same number of histidines in their sequence the H6$^1$-C20 formed the most stable complexes with siRNA resistant to proteinase K. However, in the downregulation of the target gene expression, complexes formed with it did not have the highest bioactivity (FIG. 1). Intriguingly, the complexes with H6$^1$-C18, that had higher bioactivity, had similar stability as complexes formed with NF70. There are two forces that could be accounted for this, the hydrophobicity and fatty acid length in the peptide N-terminus and the position of the histidines in the peptide sequence. Based on this, the uninterrupted histidine sequence in H6$^1$ analogue may stabilize or strengthen the interactions with the cargo (H6$^1$-C20 vs H6-C20) whereas the shorter fatty acid may result in more dynamic particle (H6$^1$-C18 vs H6$^1$-C20) (FIG. 4B). All H6 analogs with longer fatty acids were able to form complexes with siRNA as indicated by the inaccessibility of siRNA before addition of proteinase. Again, the resistance to enzymatic degradation increase is correlated with the increase of fatty acid length (FIG. 4D). CPPs have to be able to release siRNA at the destination, for it to bind to its partner and induce RNAi. Optimal stability to degradation and dissociation are therefore a prelude for this to take place.

Figure 8:
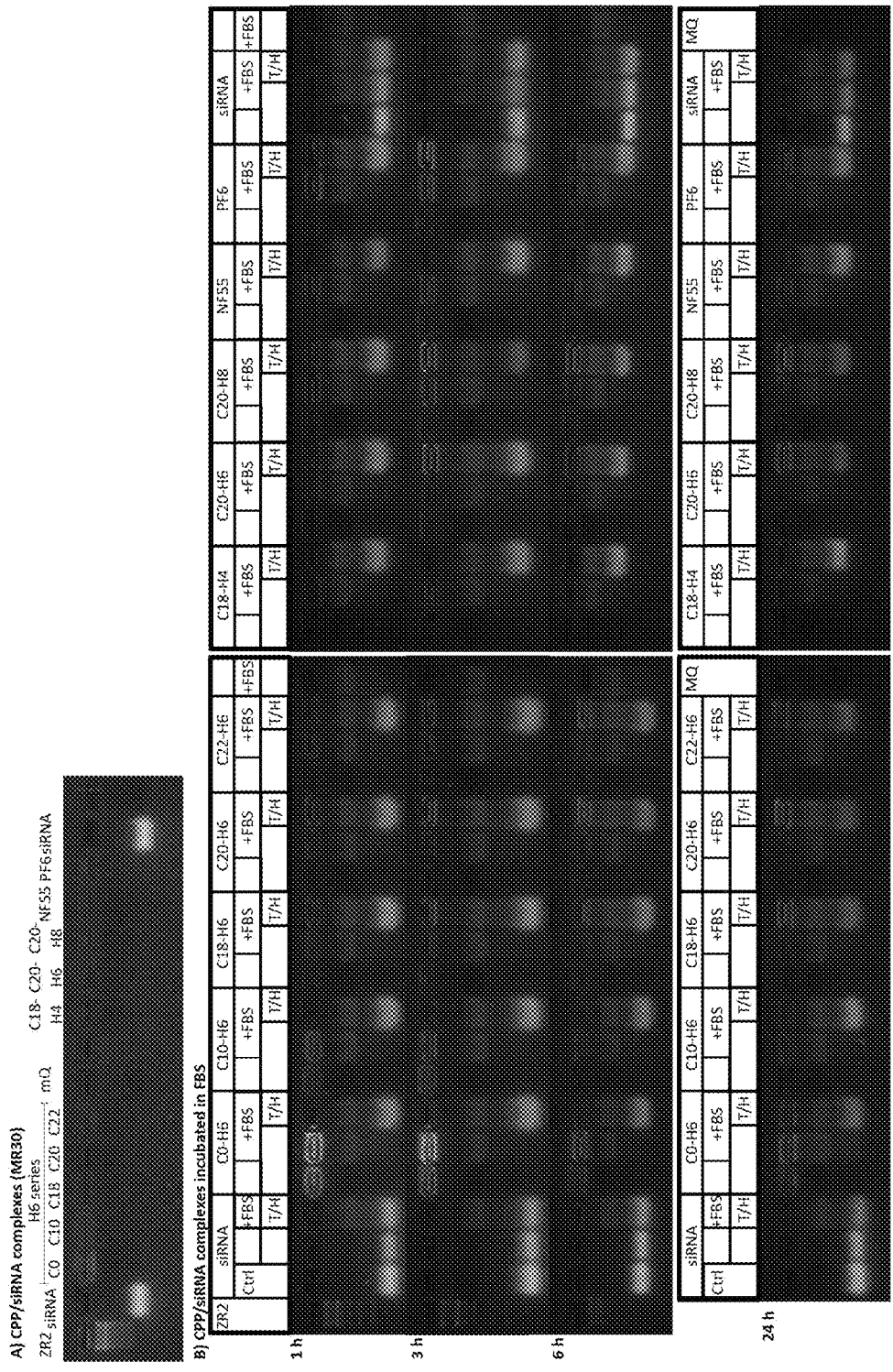
FIG. 8 shows formation and dissociation/degradation of CPP/siRNA particles, and aggregation of nanoparticles in the presence of FBS. A) CPP/siRNA complexes formed at MR30, and B) stability of CPP/siRNA complexes to FBS (50%) assessed on agarose; C) to F) show aggregation of CPP/siRNA complexes in the presence of FBS compared to particles in mQ water, assessed by absorption at $\lambda=410$ nm.
Figure 8:
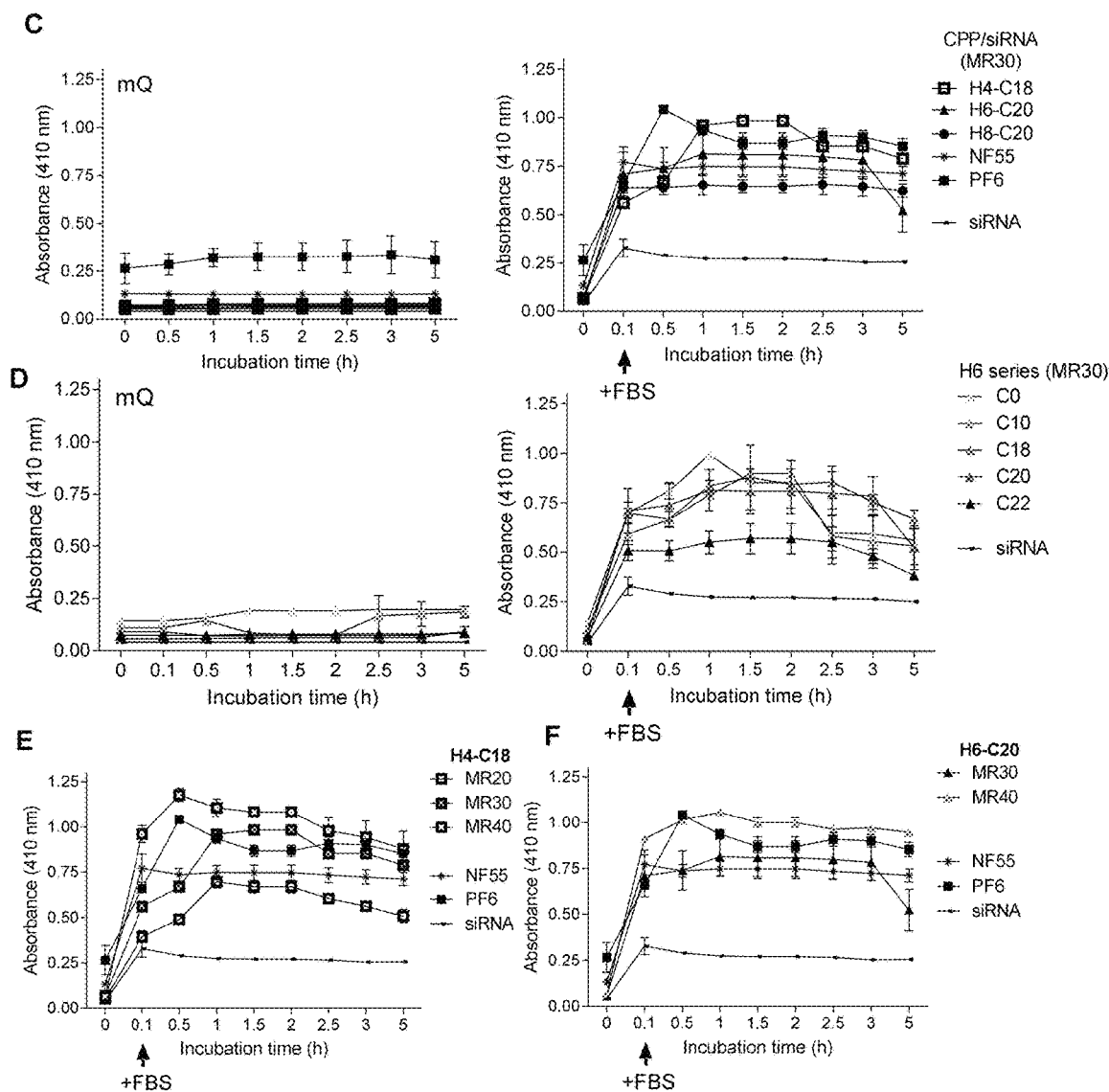

Interestingly, the addition of FBS (1:1 FBS to complex solution ratio) and the following incubation at 37° C. did not lead to the degradation of complexes as indicated by the lack of additional smear or band (FIGS. 8A and B). This could be explained by firstly the other interactions with serum components, that make the complexes inaccessible for the degrading enzymes, and secondly, the release cannot be assessed due to large aggregates that are not able to freely move in the gel (FIG. 8C-F).

Example 4

Figure 5:
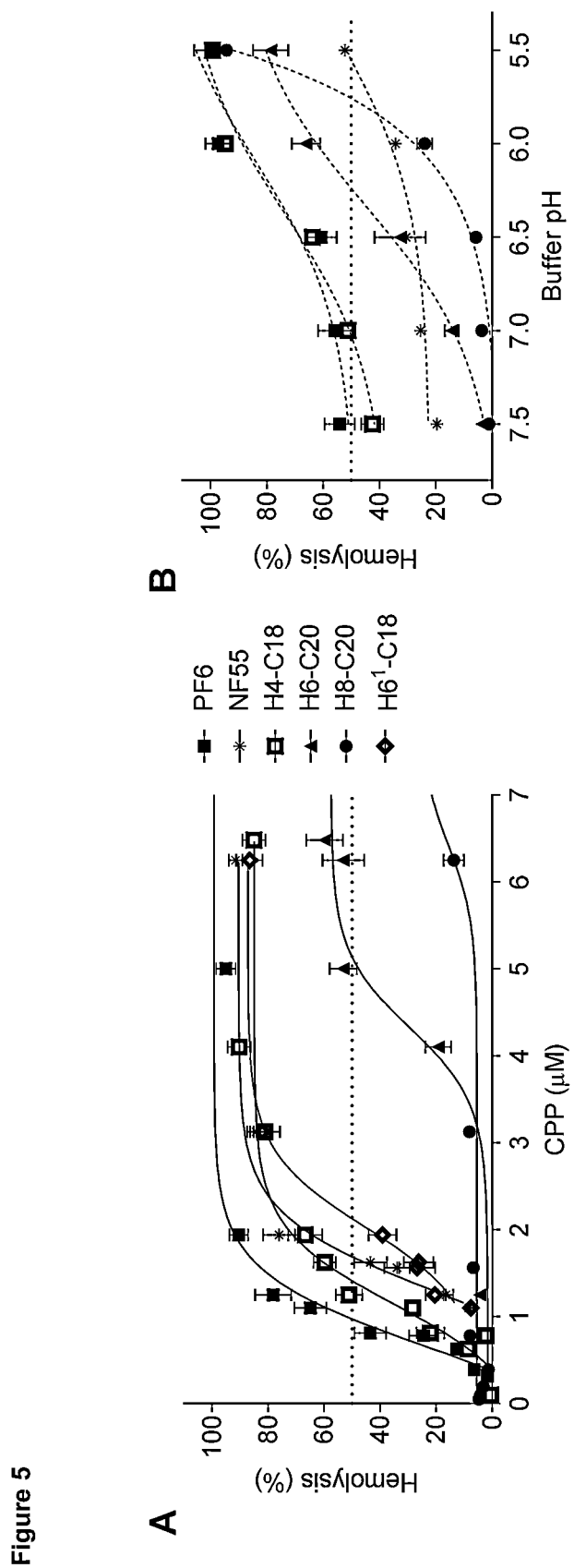
FIG. 5 shows membrane activity of CPPs assessed by haemolytic activity on murine red blood cells compared to cells treated with 0.1% Triton X-100 (100% haemolysis) or 5% glucose (0%); A) Hemolysis of cells after addition of CPP solutions at concentration range 0-6.5 uM; B) Hemolysis of red blood cells in buffers with different pH ranging from 5.5-7.5, modelling endosomolytic activity of CPPs.
Figure 9:
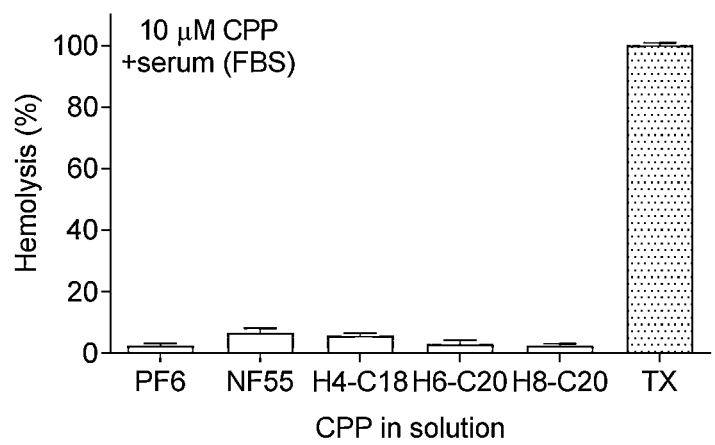
FIG. 9 shows lack of membrane haemolytic toxicity on murine red blood cells of CPPs in the presence of FBS.
Figure 10:
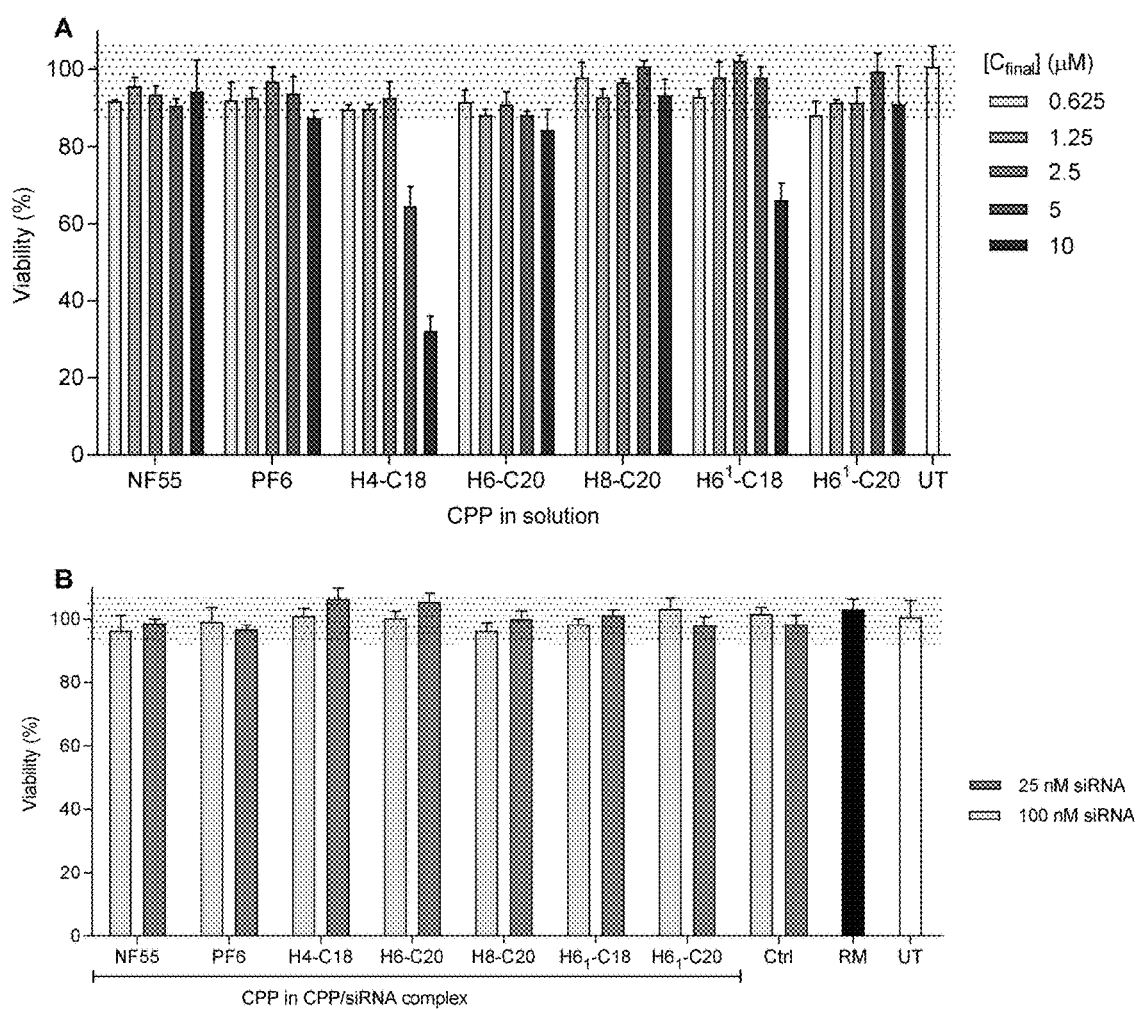
FIG. 10 shows MTS based toxicity assay on cells compared to viability of untreated cells (100%). A) Viability of cells after addition of CPP solutions in concentration range from 0.625 to 10 uM. B) Viability of cells after treatment with CPP/siRNA complexes formed at MR30 and with siRNA final concentration 25 nM or 100 nM.

Hemolytic activity of histidine-containing CPPs is lower than of PF6 and their membrane activity depends on the pH We used red blood cells (RBC) to assess the membrane activity of our peptides. Red blood cells contain hemoglobin that upon damage of cell membrane is released to the extracellular medium and can easily be quantified and the amount of released hemoglobin correlated with the number of damaged cells. Out of tested peptides PF6 was the most hemolytic, with the concentration where 50% of cells were broken (HC50) of about 1 uM peptide concentration. Interestingly H4-C18 was more hemolytic than its parent peptide NF55. For H6-C20 the HC50 concentration was 2.5 times higher than that of NF55. Comparison of H6-C20 and H6$^1$-C20 that both have six histidines, shows that the hemolytic activity for H6$^1$-C20 was significantly higher, probably due to the difference of histidine distribution in the sequence. In H6$^1$-C20, the positive charges form histidines are distributed as one block, whereas in H6-C20 they are interrupted by tyrosine. H8-C20 was less hemolytic than that of other peptides. The highest tested concentration of peptide was 10 uM that is significantly higher than the concentration we use in vitro (MR40 1 or 4 uM peptide) (FIG. 5A). It should be noted, that we tested free peptide in this assay. Addition of siRNA to the peptide solution and formation of the respective complexes decreases the hemolytic activity approximately two fold (Table 2), suggesting that the membrane activity could be mediated by the free or accessible CPP that has not been neutralized by the interaction with the negatively charged siRNA. The addition of FBS decreases significantly the hemolytic activity of the peptides (FIG. 9) indicating that several different mechanisms lead to the entry of the peptide or peptide/siRNA complexes into the cells. MTS toxicity assay on cells showed that most of the used CPP/siRNA complexes were not toxic to cells (FIG. 10B). The toxicity of free peptide was higher, and NF71 was considerably more toxic to cells starting from 5 uM concentrations and H6$^1$-C18 was toxic at 10 uM concentrations (FIG. 10A) than other histidine-containing CPPs.

TABLE 2

Average haemolytic concentration (HC50) of free peptide and CPP/siRNA complexes formatted at MR30.

| | HC50 (uM) | |
|---|---|---|
| CPP | Free peptide | CPP/siRNA complex (peptide concentration) |
| NF55 | 1.7 | 3.2 |
| PF6 | 0.9 | 2.1 |
| H4-C18 | 1.2 | 2.5 |
| H6-C20 | 4.3 | 8.3 |
| H8-C20 | >10 | nd |

To analyze the endosomolytic activity of histidine containing pH sensitive CPPs we chose the peptide concentration that is equal to peptide concentration used for CPP/siRNA complex at MR30 (peptide concentration 0.75 uM at 25 nM siRNA concentration) and kept it constant. Instead we changed the pH of the buffer surrounding RBC. The positive charge of histidine containing peptides increases when the pH decreases. Analogous pH decrease takes place in endosomal vesicles upon maturation, being more prominent in late endosomes and lysosomes. As expected, NF55 was the least influenced by the pH decrease and hemolytic activity only increased at pH 5.5 by 25% (FIG. 5B). The highest pH dependent increase of hemolytic activity exhibited peptide NF72. It had almost no effect at physiologic pH, but lysed almost all cells at pH 5.5 and its hemolytic activity started to increase already at pH 6.0. Similar tendency was also detected for NF70, but the increase was less substantial. The hemolytic effect of H6$^1$-C20 also increased at lower pH, but it was markedly hemolytic already at pH 7.5. It should be noted that the damage of RBC membranes was significantly higher in lower pH buffer even in case of negative control, i.e. peptide-free solution (1×PBS and glucose, pH 5.5) (FIG. 5B).

Example 5

NF70/siRNA complexes against blood coagulation factor VII are able to mediate downregulation of the target gene in vivo We aimed to optimize the physico-chemical properties of the CPP in the CPP/cargo complexes for the efficient delivery of the siRNA to the tissues and cell insides. For this, the association between the CPP and the siRNA must be stable enough to form complexes and to protect the siRNA from premature degradation and dissociation, but optimal for the release of the cargo at the intracellular target site. We investigated the effect of the number of histidines in the peptide sequence, their position and distribution in the N-terminal peptide part and also the effect of the N-terminal fatty acid length. We concluded that the length of the fatty acid considerably affected the nanoparticle formation, size and stability, and the final biological effect gained from the delivered cargo. There is an optimal length of fatty acid for each histidine-containing CPP set. For siRNA delivery, the longest tested FA did not translate into the highest downregulation from the delivered cargo. This can be linked to the higher stability of the CPP/siRNA complexes formed with peptides where FA C22 was used, that may hinder the release of the siRNA and its intended effect. A 20-40 nm size nanoparticle (measured in TEM) was able to mediate higher bioeffect than more compactly packaged nanoparticles with FA C22 peptides. Although the H-peptides did not form perfectly spherical particles with siRNA, they are able to mediate as efficient downregulation in vitro as PF6/siRNA particles.

Figure 11:
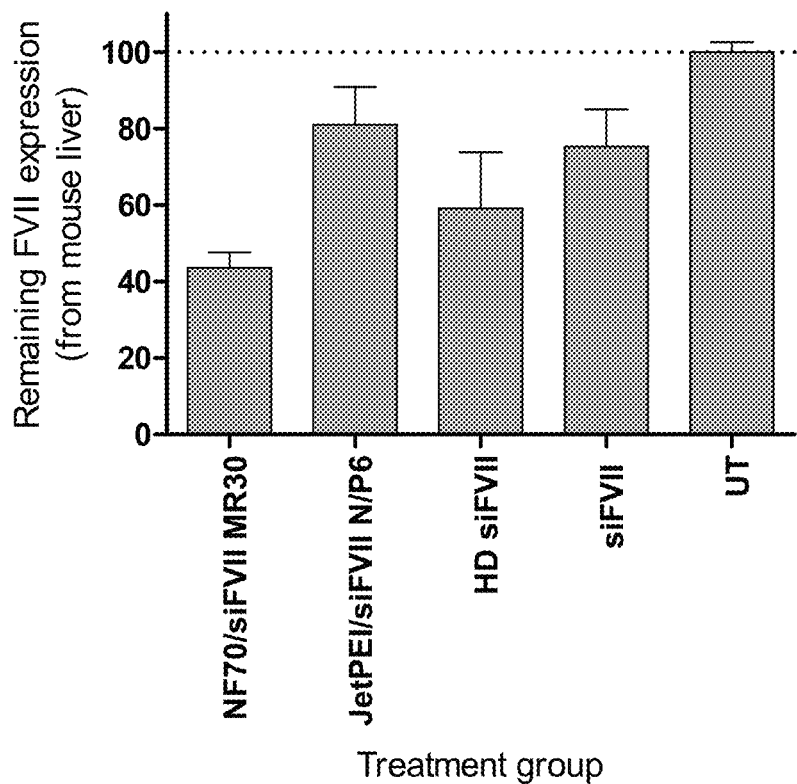
FIG. 11 shows results of downregulation of murine blood coagulation factor VII mRNA levels with siRNA against FVII and CPP/siRNA complexes. Analysis performed on mouse liver tissues 48 h post treatment and assessed by qRT-PCR. Results expressed as percentage compared to levels in untreated mice livers.

The increase in the number of histidines increases the pH-buffering ability of the peptide, although for delivery purposes there might be a cutoff for the histidine chain length, as H8 analogs were not as efficient as H6 or H4 analogs. The hemolytic concentration of histidine-containing peptides significantly decreased depending on the number of histidines in the peptide sequence when pH of the buffer was lowered from pH 7.5 to pH 5.5, indicating a pH-dependent increase in membrane activity. The downregulation of a reporter gene on cells in buffer was also pH-dependent for CPP/siRNA complexes formed with PF6 and histidine-containing CPPs. Out of the designed CPPs, two analogs NF71 and NF70 were able to deliver siRNA efficiently to the cell insides and release the cargo siRNA. The stability of particles formed between the CPP and the siRNA were not the most stable with these peptides, but the desired bioeffect was significantly higher compared to other histidine-containing analogs. The IC50 for NF71/siLuc2 nanoparticles was lower (6.8 nM at MR30) than that of efficient pH-sensitive siRNA delivery vector PepFect6 (10.4 nM at MR30), but due to its hemolytic activity and effect on cell proliferation when used at higher concentrations, we excluded it from in vivo testing. The second best peptide in vitro tests, with a 3.6 higher hemolytic concentration, IC50 14.8 nM at MR30, and lower cell toxicity, NF70, was able to deliver siRNA to mouse liver in vivo and already after single injection resulted in an almost 60% downregulation of the target (FIG. 11). The potential of using NF70 as a siRNA delivery vector in vivo was assessed by using siRNA against blood coagulation factor VII mRNA. Enzyme factor VII a vitamin K dependent protein in the blood coagulation cascade, and is mainly synthesized in the liver cells. It has a short half-life compared to other clotting factors. Compared to untreated mice, only approximately 40% of RNA levels preserved in NF70/siFVII treated mice. Compared to siRNA delivery with nanogel nanoparticles, we were able to achieve 30% downregulation, compared to siRNA treated group, with significantly lower siRNA dose (1.6 mg/kg vs 4 mg/kg). Compared to free siRNA, and commercially available in vivo transfection reagent In vivo JetPEI (Polyplus, Germany) at N/P6 the NF70/siFVII complexes were able to mediate higher downregulation effect at the same 1.6 mg/kg dose.

Example 6

To demonstrate the difference in efficiency between complexes having C-terminal histidine modifications and complexes having N-terminal modifications, CPP/siRNA complexes were formed and luminescence from luciferin-luciferase reaction was determined.

The experiment was carried out in serum containing media (10% FBS). CPP/siRNA complexes were formed at different molar ratios with siRNA concentration kept constant (50 nM in transfection media). Luminescence from luciferin-luciferase reaction was measured at 24 hours post-treatment from cell lysate. Results were normalized to protein content and luminescence values from untreated cells (100%).

C-terminal histidine modifications (NF73, NF74) reduced peptide efficiency compared to N-terminal modifications (NF714, NF71)

Figure 12:
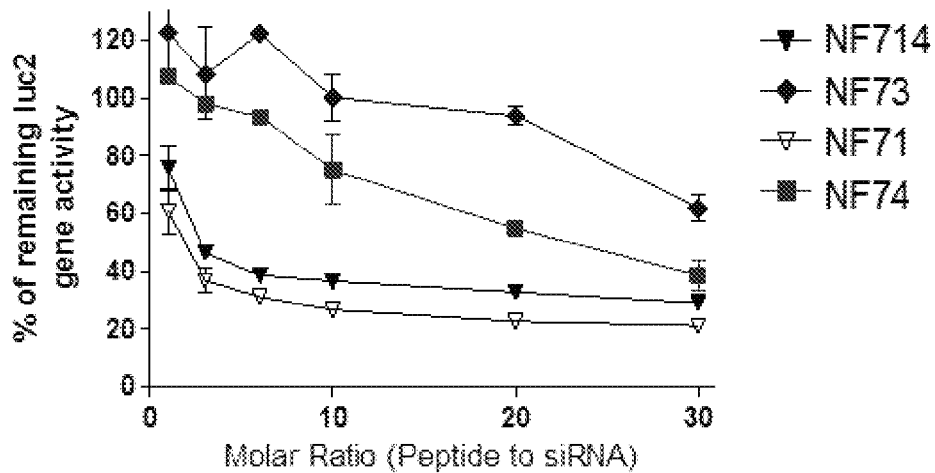
FIG. 12 shows the downregulation of luciferase activity with luciferase siRNA containing CPP/siRNA complexes. Luminescence from luciferin-luciferase reaction was measured 24 h post-treatment from cell lysate.

The C-terminal histidine substitutions (NF73, NF74) demonstrated significantly reduced efficiency at all the peptide concentrations tested as compared to the N-terminal modified peptides (NF714, NF71), see FIG. 12.

Example 7

Histidine containing peptides are efficient delivery vectors for pDNA

Figure 14:
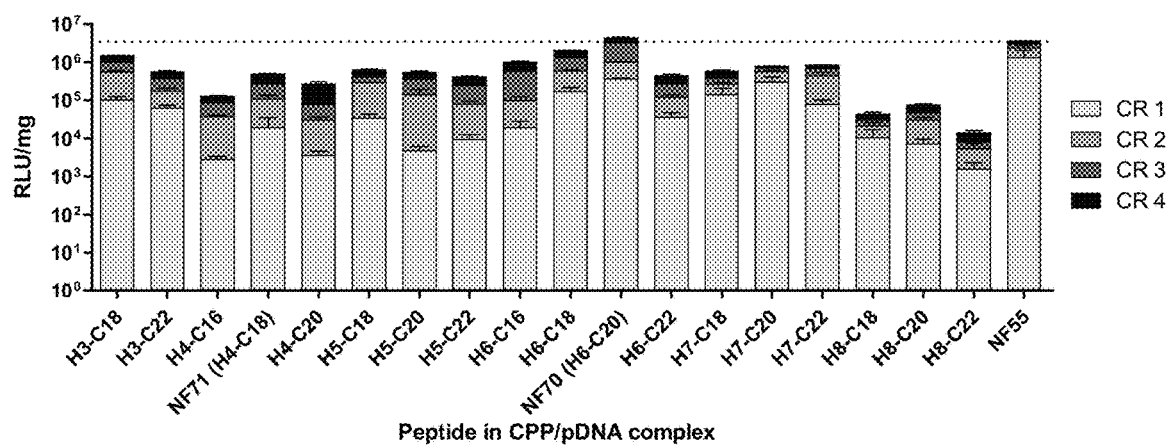
FIG. 14 shows the ability of CPPs to deliver pDNA into cells. Transfection of CPP/pDNA complexes at various charge ratios (peptide over plasmid). Results are normalised to protein content.

All the histidine containing CPPs were compared for their efficacy to deliver pDNA into CHO cells in serum containing medium. The concentration of the CPP was varied from CR1 to CR4 and luciferase encoding plasmid was used. 24 h after transfection luciferase expression was measured (FIG. 14).

NF70 (H6-C20), a novel peptide with 6 histidines, was able to deliver pDNA with high efficiency and achieved gene expression which was similar to that of the parental peptide NF55. Furthermore, NF702 (H6-C18)/pDNA transfection almost yielded the same gene expression level as that of NF70 and NF55, showing that CPPs with 6 histidines have a good potential for gene delivery in vitro.

Besides these CPPs several other novel histidine containing peptides e.g. NF725 (H3-C18), NF727 (H3-C22), NF71 (H4-C18), NF716 (H5-C20) and NF702 (H6-C18) turned out to be promising vectors for pDNA transfection. Although the reached gene expression levels were less than with NF55, the novel CPP are pH dependent which gives them several advantages in hard to transfect cells.

Example 8

Histidine containing CPPs for systemic gene delivery in vivo

Based on the results of in vitro assays, we chose the most potent peptides in pDNA transfection for in vivo testing; NF70 (H6-C20), NF71 (H4-C18) and NF725 (H3-C18).

Figure 15:
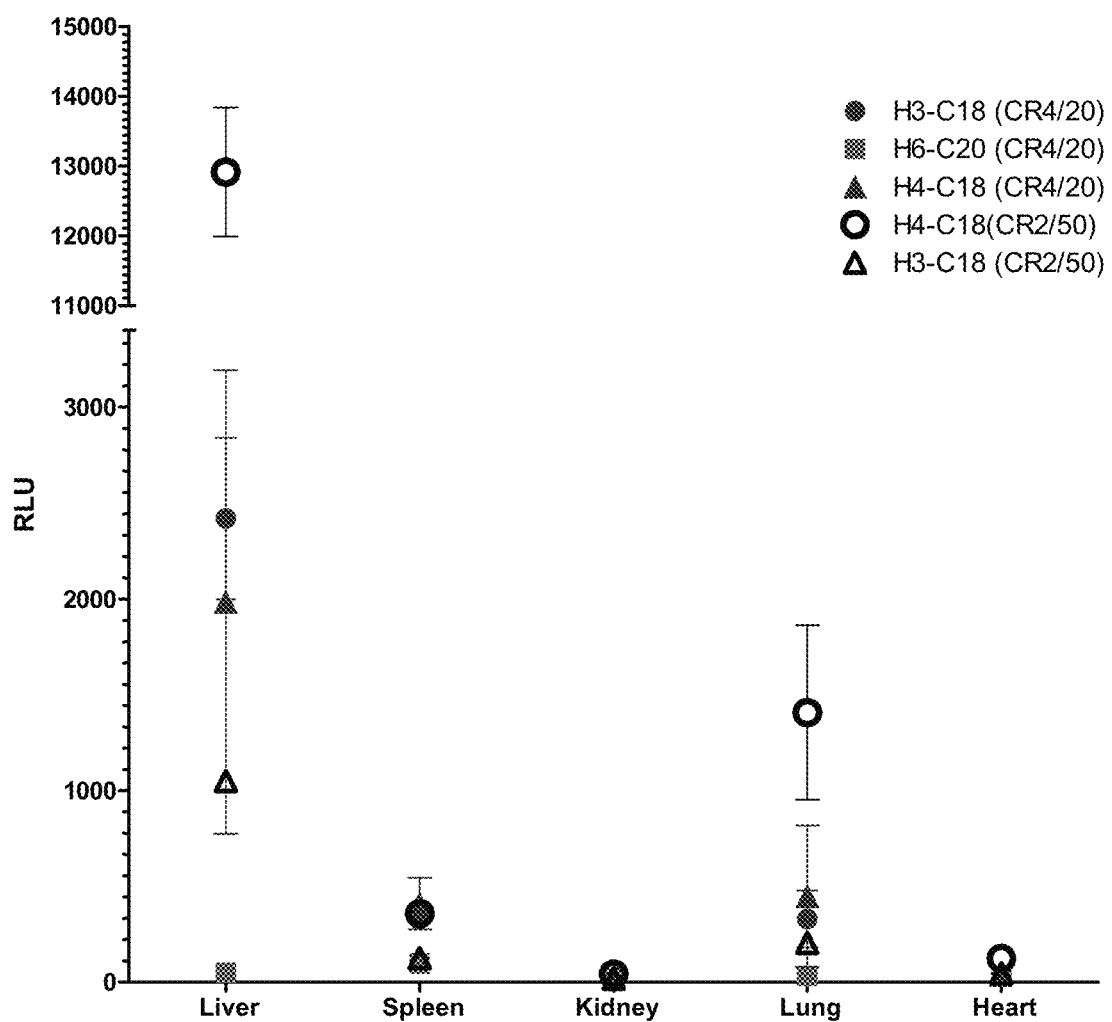
FIG. 15 shows expression of marker gene in the organs of BALB/c mice transfected by CPP/pDNA nanoparticles. Results expressed as percentage compared to levels in organs of untreated mice.

Gene expression levels were evaluated post mortem 24 h after injecting NF/pDNA complexes i.v. into tail vein. Each animal received a single 200 ul i.v. injection of pDNA, formulated with NFs at CR2 or CR4 with 50 µg or 20 µg of pDNA. After 24 h mice were sacrificed using cervical dislocation and whole organs were harvested and homogenized (FIG. 15).

In NF71 (H4-C18)/pDNA treated animals we detected high reporter gene expression in liver and lungs. Besides these organs, gene expression was found in spleen and heart. Interestingly transfection levels were 7-fold higher in liver and 3-fold in lungs at CR2 compared to CR4.

NF725 (H3-C18)/pDNA injection lead to high gene expression level in liver. Still lower gene expression was detected in lungs and spleen. With this CPP, the transfection level was higher at CR4 than CR2.

Unexpectedly NF70 (H6-C20) that was very efficient for delivering pDNA in vitro showed very low transfection levels in vivo.

These results confirm that after dose optimisation of histidine containing CPPs, NF71 (H4-C18) and NF725 (H3-C18) have high potential for systemic gene delivery.

Example 9

Figure 16:
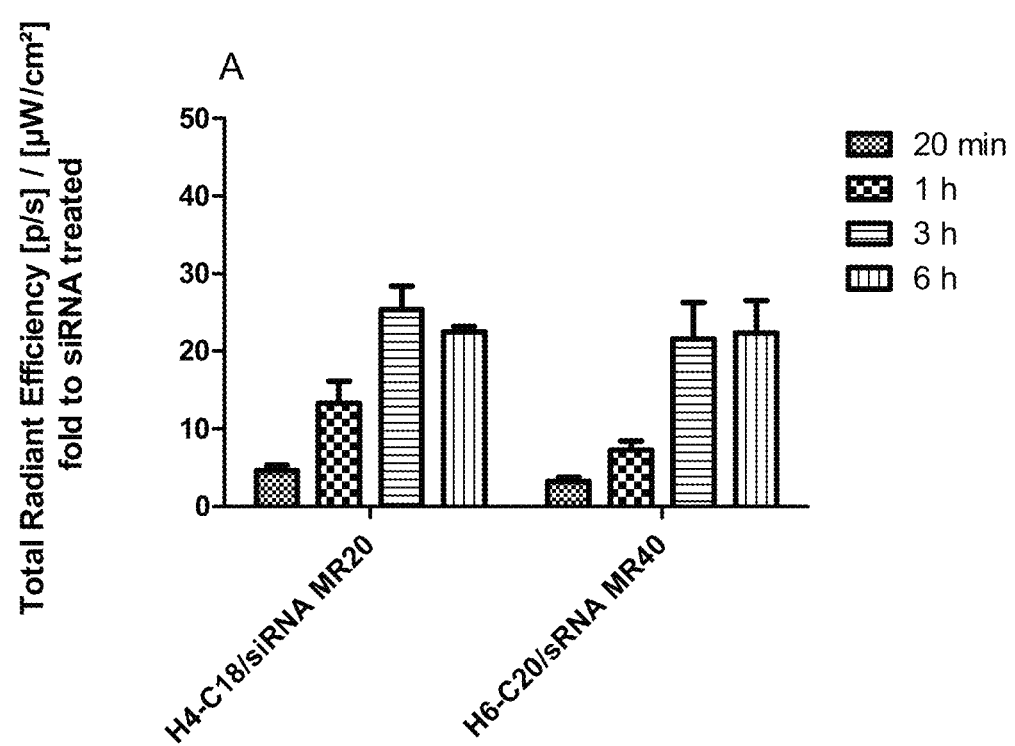
FIG. 16 shows His-containing peptide/Cy5-siRNA nanoparticles accumulation into subcutaneous A) U87 and B) HT-1080 tumors after systematic injection. Results are normalized to Cy5-siRNA treated mice.
Figure 16:
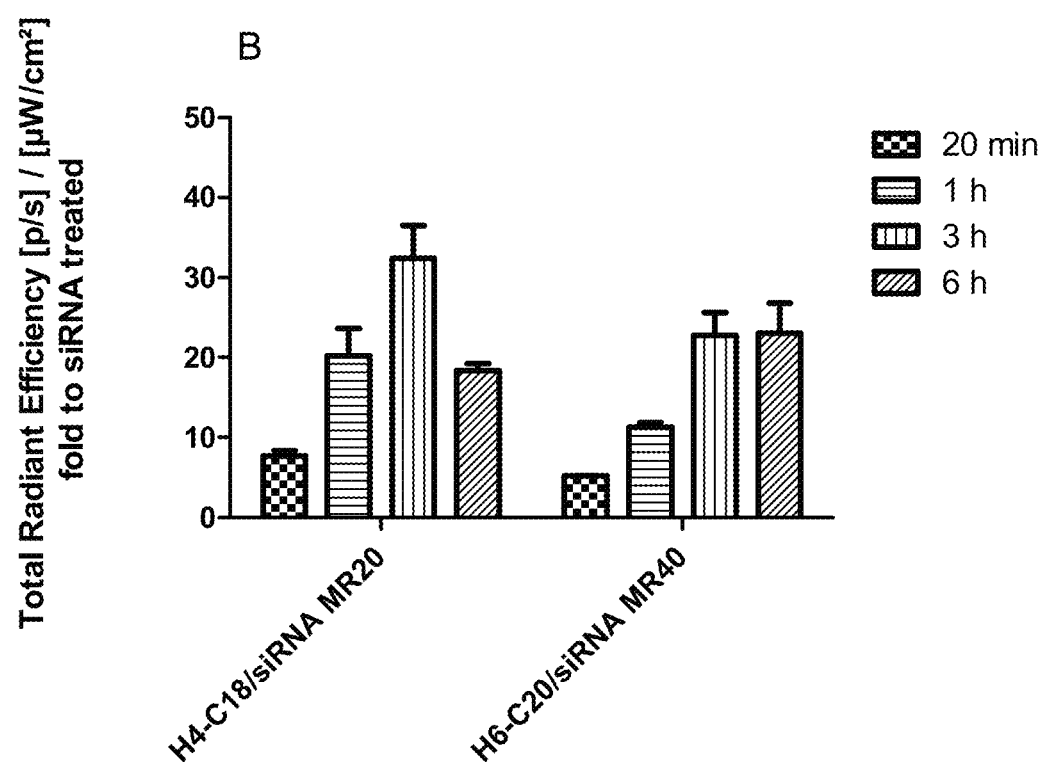

H4-C18/Cy5-siRNA and H6-C20/Cy5-siRNA nanoparticles accumulate into tumor region after systematic delivery in vivo (FIG. 16)

In order to study accumulation of CPP/cy-5 siRNA nanoparticles in tumor tissue, nude mice bearing U87 or HT-1080 tumor xenografts were injected with H4-C18/Cy5-siRNA or H6-C20/Cy5-siRNA complexes at MR20 or MR40 respectively via tail vein. Cy5 fluorescence values were acquired from the tumor region at different time points and normalized to the value of naked Cy5-siRNA in tumor at the corresponding time point.

H4-C18/Cy5-siRNA and H6-C20/Cy5-siRNA complexes accumulation in both U87 (FIG. 16 A) or HT-1080 (FIG. 16 B) tumor regions was more than 25-fold higher than for naked SiRNA. H4-C18/Cy5-siRNA nanoparticles peaked at 3 h, reaching 27-fold in U87 and 37-fold in HT-1080 tumor. H6-C20/Cy5-siRNA nanoparticles accumulation in both tumors was more than 25-fold at 3 and 6 h. As no declining of fluorescence signal was detected at 6 h, we may assume that H6-C20/Cy5-siRNA nanoparticles stay in tumor for a longer period of time. These results indicate that his containing CPP/siRNA nanoparticles reach tumor tissue after systematic administration via tail vein and stay there for more than 6 hours period of time.

CONCLUSIONS

In this work we have demonstrated an appealing, simple and efficient strategy to enhance and optimize the delivery efficacy and pH-sensitivity of a CPP-based delivery vector for cargo delivery, particularly siRNA. We designed and tested pH-sensitive histidine-containing analogs of NickFect55 with the ability to associate with siRNA as an exemplary cargo, and to form stable nanoparticles, and able to release the cargo in order to it to take its intended effect.

We show the effect of amino acid histidine number, position and distribution in the peptide sequence and also the significance of a fatty acid modification and its length to the assembly and characteristics of CPP/siRNA nanoparticles.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents, patent applications and references mentioned throughout the specification of the present invention are herein incorporated in their entirety by reference.

The invention embraces all combinations of preferred and more preferred groups and suitable and more suitable groups and embodiments of groups recited above.

The invention claimed is:

1. A membrane-permeable construct for transport of cargo across a lipid membrane and subsequent delivery of cargo into cells, wherein the construct comprises a cell penetrating amino acid sequence and a fatty acid chain attached to the N terminus thereof, wherein the cell penetrating amino acid sequence comprises the sequence of SEQ ID NO: 1 having an N9L amino acid substitution;

wherein the cell penetrating amino acid sequence comprises two or more histidine residues by substitution at positions 1 to 5 of SEQ ID NO: 1 and/or addition to its N-terminus, wherein the construct is selected from SEQ ID NO: 2 with a fatty acid chain having 18 or 20 carbon atoms; SEQ ID NO: 3 with a fatty acid chain having 20 carbon atoms; SEQ ID NO: 4 with a fatty acid chain having 18 carbon atoms; and SEQ ID NO: 5 with a fatty acid chain having 20 carbon atoms.

2. The construct according to claim 1, wherein the construct (i) further comprises a cargo covalently attached thereto or (ii) further comprises a cargo covalently attached thereto and at least one imaging agent and/or labelling molecule.

3. The construct according to claim 2, wherein the cargo is a peptide, a protein or a non-peptidic pharmaceutical.

4. A complex comprising a construct according to claim 1 and (i) a cargo non-covalently interacting therewith or (ii) a cargo non-covalently interacting therewith and said complex further comprises at least one imaging agent and/or labelling molecule.

5. The complex according to claim 4, wherein the complex forms a nanoparticle.

6. The complex according to claim 4, wherein the cargo is selected from a group consisting of oligonucleotides, a peptide, a protein and a non-peptidic pharmaceutical.

7. A pharmaceutical composition comprising the construct of claim 1 and a pharmaceutically acceptable carrier.

8. The complex according to claim 4, wherein the cargo is nucleic acids and is selected from a group consisting of single-stranded oligonucleotides, double-stranded oligonucleotides and cyclic DNA.

9. The complex according to claim 8, wherein the cargo is double-stranded oligonucleotides and is selected from siRNA, shRNA, microRNA and decoy DNA.

10. The complex according to claim 4, wherein the cargo is nucleic acids and is selected from DNA, siRNA, microRNA, shRNA, antisense oligonucleotides, decoy DNA, plasmid DNA and mRNA.

11. The complex according to claim 6, wherein the cargo is selected from a group consisting of single-stranded oligonucleotides, double-stranded oligonucleotides and cyclic DNA.

* * * * *

SEQUENCE LISTING

```
<160> NUMBER OF SEQ ID NOS: 22

<210> SEQ ID NO 1
<211> LENGTH: 21
<212> TYPE: PRT
<213> ORGANISM: Artificial Sequence
<220> FEATURE:
<223> OTHER INFORMATION: Cell penetrating amino acid sequence; NF55
<220> FEATURE:
<221> NAME/KEY: MISC_FEATURE
<222> LOCATION: (7)..(7)
<223> OTHER INFORMATION: Xaa = Orn; the peptide continues from the side
      chain amino group and not from the alpha-amino group

<400> SEQUENCE: 1

Ala Gly Tyr Leu Leu Gly Xaa Ile Asn Leu Lys Ala Leu Ala Ala Leu
1               5                   10                  15

Ala Lys Ala Ile Leu
            20

<210> SEQ ID NO 2
<211> LENGTH: 21
```

```
<212> TYPE: PRT
<213> ORGANISM: Artificial Sequence
<220> FEATURE:
<223> OTHER INFORMATION: Cell penetrating amino acid sequence; NF71,
      N712, NF713, NF717
<220> FEATURE:
<221> NAME/KEY: MISC_FEATURE
<222> LOCATION: (7)..(7)
<223> OTHER INFORMATION: Xaa = Orn; the peptide continues from the side
      chain amino group and not from the alpha-amino group

<400> SEQUENCE: 2

His His Tyr His His Gly Xaa Ile Leu Leu Lys Ala Leu Lys Ala Leu
1               5                   10                  15

Ala Lys Ala Ile Leu
            20

<210> SEQ ID NO 3
<211> LENGTH: 23
<212> TYPE: PRT
<213> ORGANISM: Artificial Sequence
<220> FEATURE:
<223> OTHER INFORMATION: Cell penetrating amino acid sequence; NF70,
      NF703, NF702, NF701, NF700, NF711
<220> FEATURE:
<221> NAME/KEY: MISC_FEATURE
<222> LOCATION: (9)..(9)
<223> OTHER INFORMATION: Xaa = Orn; the peptide continues from the side
      chain amino group and not from the alpha-amino group

<400> SEQUENCE: 3

His His His His Tyr His His Gly Xaa Ile Leu Leu Lys Ala Leu Lys
1               5                   10                  15

Ala Leu Ala Lys Ala Ile Leu
            20

<210> SEQ ID NO 4
<211> LENGTH: 22
<212> TYPE: PRT
<213> ORGANISM: Artificial Sequence
<220> FEATURE:
<223> OTHER INFORMATION: Cell penetrating amino acid sequence; NF704,
      NF705, NF706
<220> FEATURE:
<221> NAME/KEY: MISC_FEATURE
<222> LOCATION: (8)..(8)
<223> OTHER INFORMATION: Xaa = Orn; the peptide continues from the side
      chain amino group and not from the alpha-amino group

<400> SEQUENCE: 4

His His His His His His Gly Xaa Ile Leu Leu Lys Ala Leu Lys Ala
1               5                   10                  15

Leu Ala Lys Ala Ile Leu
            20

<210> SEQ ID NO 5
<211> LENGTH: 25
<212> TYPE: PRT
<213> ORGANISM: Artificial Sequence
<220> FEATURE:
<223> OTHER INFORMATION: Cell penetrating amino acid sequence; NF72,
      NF721, NF722
<220> FEATURE:
<221> NAME/KEY: MISC_FEATURE
<222> LOCATION: (11)..(11)
<223> OTHER INFORMATION: Xaa = Orn; the peptide continues from the side
      chain amino group and not from the alpha-amino group

<400> SEQUENCE: 5
```

His His His His His Tyr His His Gly Xaa Ile Leu Leu Lys Ala
1               5                   10                  15

Leu Lys Ala Leu Ala Lys Ala Ile Leu
            20                  25

<210> SEQ ID NO 6
<211> LENGTH: 20
<212> TYPE: PRT
<213> ORGANISM: Artificial Sequence
<220> FEATURE:
<223> OTHER INFORMATION: General formula of the cell penetrating amino
      acid sequence of the invention
<220> FEATURE:
<221> NAME/KEY: MISC_FEATURE
<222> LOCATION: (6)..(6)
<223> OTHER INFORMATION: Xaa = Orn; the peptide continues from the side
      chain amino group and not from the alpha-amino group

<400> SEQUENCE: 6

His Tyr His His Gly Xaa Ile Leu Leu Lys Ala Leu Lys Ala Leu Ala
1               5                   10                  15

Lys Ala Ile Leu
            20

<210> SEQ ID NO 7
<211> LENGTH: 21
<212> TYPE: DNA
<213> ORGANISM: Artificial Sequence
<220> FEATURE:
<223> OTHER INFORMATION: siRNA sense strand against luc2

<400> SEQUENCE: 7
ggacgaggac gagcacuuct t                                         21

<210> SEQ ID NO 8
<211> LENGTH: 21
<212> TYPE: RNA
<213> ORGANISM: Artificial Sequence
<220> FEATURE:
<223> OTHER INFORMATION: siRNA antisense strand against luc2

<400> SEQUENCE: 8
gaagugcucg uccucguccu u                                         21

<210> SEQ ID NO 9
<211> LENGTH: 21
<212> TYPE: RNA
<213> ORGANISM: Artificial Sequence
<220> FEATURE:
<223> OTHER INFORMATION: siRNA sense strand against GFP

<400> SEQUENCE: 9
ggcuacgucc aggagcgcac c                                         21

<210> SEQ ID NO 10
<211> LENGTH: 21
<212> TYPE: RNA
<213> ORGANISM: Artificial Sequence
<220> FEATURE:
<223> OTHER INFORMATION: siRNA antisense strand against GFP

<400> SEQUENCE: 10
ugcgcuccug gacguagccu u                                         21

<210> SEQ ID NO 11
<211> LENGTH: 21

```
<212> TYPE: DNA
<213> ORGANISM: Artificial Sequence
<220> FEATURE:
<223> OTHER INFORMATION: Mus blood coagulation factor VII forward PCR
      primer

<400> SEQUENCE: 11
acaagtctta cgtctgcttc t                                              21

<210> SEQ ID NO 12
<211> LENGTH: 21
<212> TYPE: DNA
<213> ORGANISM: Artificial Sequence
<220> FEATURE:
<223> OTHER INFORMATION: Mus blood coagulation factor VII reverse PCR
      primer

<400> SEQUENCE: 12
cacagatcag ctgctcattc t                                              21

<210> SEQ ID NO 13
<211> LENGTH: 20
<212> TYPE: DNA
<213> ORGANISM: Artificial Sequence
<220> FEATURE:
<223> OTHER INFORMATION: Mus Actin beta forward PCR primer

<400> SEQUENCE: 13
ccacacccgc caccagttcg                                                20

<210> SEQ ID NO 14
<211> LENGTH: 20
<212> TYPE: DNA
<213> ORGANISM: Artificial Sequence
<220> FEATURE:
<223> OTHER INFORMATION: Mus Actin beta reverse PCR primer

<400> SEQUENCE: 14
tacagcccgg ggagcatcgt                                                20

<210> SEQ ID NO 15
<211> LENGTH: 25
<212> TYPE: PRT
<213> ORGANISM: Artificial Sequence
<220> FEATURE:
<223> OTHER INFORMATION: Cell penetrating amino acid sequence; NF707,
      NF708, NF709
<220> FEATURE:
<221> NAME/KEY: MISC_FEATURE
<222> LOCATION: (11)..(11)
<223> OTHER INFORMATION: Xaa = Orn; the peptide continues from the side
      chain amino group and not from the alpha amino group

<400> SEQUENCE: 15

His His His His His His Tyr Leu Leu Gly Xaa Ile Leu Leu Lys Ala
1               5                   10                  15

Leu Lys Ala Leu Ala Lys Ala Ile Leu
            20                  25

<210> SEQ ID NO 16
<211> LENGTH: 21
<212> TYPE: PRT
<213> ORGANISM: Artificial Sequence
<220> FEATURE:
<223> OTHER INFORMATION: Cell penetrating amino acid sequence of Figure
      12, NF714
<220> FEATURE:
<221> NAME/KEY: MISC_FEATURE
```

```
<222> LOCATION: (7)..(7)
<223> OTHER INFORMATION: Xaa = Orn; the peptide continues from the side
      chain amino group and not from the alpha-amino group

<400> SEQUENCE: 16

His His Tyr His His Gly Xaa Ile Asn Leu Lys Ala Leu Lys Ala Leu
1               5                   10                  15

Ala Lys Ala Ile Leu
            20

<210> SEQ ID NO 17
<211> LENGTH: 21
<212> TYPE: PRT
<213> ORGANISM: Artificial Sequence
<220> FEATURE:
<223> OTHER INFORMATION: Cell penetrating amino acid sequence of Figure
      12, NF73
<220> FEATURE:
<221> NAME/KEY: MISC_FEATURE
<222> LOCATION: (7)..(7)
<223> OTHER INFORMATION: Xaa = Orn; the peptide continues from the side
      chain amino group and not from the alpha-amino group

<400> SEQUENCE: 17

Ala Gly Tyr Leu Leu Gly Xaa Ile His Leu Lys Ala His Lys Ala His
1               5                   10                  15

Ala Lys Ala His Leu
            20

<210> SEQ ID NO 18
<211> LENGTH: 21
<212> TYPE: PRT
<213> ORGANISM: Artificial Sequence
<220> FEATURE:
<223> OTHER INFORMATION: Cell penetrating amino acid sequence of Figure
      12, NF74
<220> FEATURE:
<221> NAME/KEY: MISC_FEATURE
<222> LOCATION: (7)..(7)
<223> OTHER INFORMATION: Xaa = Orn; the peptide continues from the side
      chain amino group and not from the alpha-amino group

<400> SEQUENCE: 18

Ala Gly Tyr Leu Leu Gly Xaa Ile Leu His Lys Ala His His Lys Leu
1               5                   10                  15

His Lys Ala Ile Leu
            20

<210> SEQ ID NO 19
<211> LENGTH: 20
<212> TYPE: PRT
<213> ORGANISM: Artificial Sequence
<220> FEATURE:
<223> OTHER INFORMATION: Cell penetrating amino acid sequence of the
      invention; NF725, NF726, NF727
<220> FEATURE:
<221> NAME/KEY: MISC_FEATURE
<222> LOCATION: (6)..(6)
<223> OTHER INFORMATION: Xaa = Orn; the peptide continues from the side
      chain amino group and not from the alpha-amino group

<400> SEQUENCE: 19

His Tyr His His Gly Xaa Ile Leu Leu Lys Ala Leu Lys Ala Leu Ala
1               5                   10                  15

Lys Ala Ile Leu
            20
```

```
<210> SEQ ID NO 20
<211> LENGTH: 22
<212> TYPE: PRT
<213> ORGANISM: Artificial Sequence
<220> FEATURE:
<223> OTHER INFORMATION: Cell penetrating amino acid sequence of the
      invention; NF715, NF716, NF718
<220> FEATURE:
<221> NAME/KEY: MISC_FEATURE
<222> LOCATION: (8)..(8)
<223> OTHER INFORMATION: Xaa = Orn; the peptide continues from the side
      chain amino group and not from the alpha-amino group

<400> SEQUENCE: 20

His His His Tyr His His Gly Xaa Ile Leu Leu Lys Ala Leu Lys Ala
1               5                   10                  15

Leu Ala Lys Ala Ile Leu
            20

<210> SEQ ID NO 21
<211> LENGTH: 24
<212> TYPE: PRT
<213> ORGANISM: Artificial Sequence
<220> FEATURE:
<223> OTHER INFORMATION: Cell penetrating amino acid sequence of the
      invention; NF719, NF723, NF724
<220> FEATURE:
<221> NAME/KEY: MISC_FEATURE
<222> LOCATION: (10)..(10)
<223> OTHER INFORMATION: Xaa = Orn; the peptide continues from the side
      chain amino group and not from the alpha-amino group

<400> SEQUENCE: 21

His His His His His Tyr His His Gly Xaa Ile Leu Leu Lys Ala Leu
1               5                   10                  15

Lys Ala Leu Ala Lys Ala Ile Leu
            20

<210> SEQ ID NO 22
<211> LENGTH: 21
<212> TYPE: PRT
<213> ORGANISM: Artificial Sequence
<220> FEATURE:
<223> OTHER INFORMATION: artificial sequence
<220> FEATURE:
<221> NAME/KEY: MISC_FEATURE
<222> LOCATION: (7)..(7)
<223> OTHER INFORMATION: Three Lys added to Lys7 of the peptide to form
      lysine tree

<400> SEQUENCE: 22

Ala Gly Tyr Leu Leu Gly Lys Ile Asn Leu Lys Ala Leu Ala Ala Leu
1               5                   10                  15

Ala Lys Lys Ile Leu
            20
```